(12) United States Patent
Voronina et al.

(10) Patent No.: US 10,314,296 B2
(45) Date of Patent: Jun. 11, 2019

(54) GENETICALLY MODIFIED MAJOR HISTOCOMPATIBILITY COMPLEX MICE

(71) Applicant: Regeneron Pharmaceuticals, Inc., Tarrytown, NY (US)

(72) Inventors: Vera Voronina, Sleepy Hollow, NY (US); Cagan Gurer, Chappaqua, NY (US); Andrew J. Murphy, Croton-on-Hudson, NY (US); Lynn Macdonald, Harrison, NY (US); Yingzi Xue, Ardsley, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 15/839,655

(22) Filed: Dec. 12, 2017

(65) Prior Publication Data

US 2018/0116190 A1 May 3, 2018

Related U.S. Application Data

(63) Continuation of application No. 14/830,464, filed on Aug. 19, 2015, now abandoned, which is a continuation-in-part of application No. 14/185,316, filed on Feb. 20, 2014, now Pat. No. 10,154,658.

(60) Provisional application No. 62/039,333, filed on Aug. 19, 2014, provisional application No. 61/767,811, filed on Feb. 22, 2013.

(51) Int. Cl.
| | |
|---|---|
| *A01K 67/00* | (2006.01) |
| *A01K 67/027* | (2006.01) |
| *C07K 14/74* | (2006.01) |
| *C07K 14/73* | (2006.01) |
| *C07K 14/705* | (2006.01) |
| *C12N 15/85* | (2006.01) |

(52) U.S. Cl.
CPC ...... *A01K 67/0271* (2013.01); *A01K 67/0278* (2013.01); *C07K 14/70539* (2013.01); *A01K 2207/15* (2013.01); *A01K 2217/072* (2013.01); *A01K 2227/105* (2013.01); *A01K 2267/03* (2013.01); *C07K 14/70514* (2013.01); *C07K 14/70517* (2013.01); *C12N 15/8509* (2013.01)

(58) Field of Classification Search
CPC .................................................. A01K 67/0271
See application file for complete search history.

(56) References Cited

U.S. PATENT DOCUMENTS

| | | | |
|---|---|---|---|
| 5,413,923 A | 5/1995 | Kucherlapati et al. | |
| 5,416,260 A | 5/1995 | Koller et al. | |
| 5,574,205 A | 11/1996 | Kucherlapati et al. | |
| 5,644,065 A | 7/1997 | Benoist et al. | |
| 5,859,312 A | 1/1999 | Littman et al. | |
| 5,942,435 A | 8/1999 | Wheeler | |
| 5,965,787 A | 10/1999 | Luthra et al. | |
| 6,002,066 A | 12/1999 | Leung et al. | |
| 6,139,835 A | 10/2000 | Kucherlapati et al. | |
| 6,150,584 A | 11/2000 | Kucherlapati et al. | |
| 6,270,772 B1 | 8/2001 | Burrows et al. | |
| 6,372,955 B1 | 4/2002 | Karlsson et al. | |
| 6,514,752 B1 | 2/2003 | Kucherlapati et al. | |
| 6,586,251 B2 | 7/2003 | Economides et al. | |
| 6,596,541 B2 | 7/2003 | Murphy et al. | |
| 6,815,171 B2 | 11/2004 | Burrows et al. | |
| 7,105,348 B2 | 9/2006 | Murphy et al. | |
| 7,265,218 B2 | 9/2007 | Burrows et al. | |
| 7,294,754 B2 | 11/2007 | Poueymirou et al. | |
| 7,339,089 B2 | 3/2008 | Gotch | |
| 7,663,017 B2 | 2/2010 | Lone et al. | |
| 7,745,690 B2 | 6/2010 | Kanazawa et al. | |
| 8,178,653 B2 | 5/2012 | Tureci et al. | |
| 8,847,005 B2 | 9/2014 | Macdonald et al. | |
| 9,043,996 B2 | 6/2015 | Macdonald et al. | |
| 9,585,373 B2 | 3/2017 | Macdonald et al. | |
| 9,591,835 B2 | 3/2017 | Macdonald et al. | |
| 9,615,550 B2 | 4/2017 | Macdonald et al. | |
| 2002/0164721 A1 | 11/2002 | Firat et al. | |
| 2003/0093818 A1 | 5/2003 | Belmont et al. | |
| 2003/0124524 A1 | 7/2003 | Kornman et al. | |
| 2005/0050580 A1 | 3/2005 | Gotch et al. | |
| 2005/0066375 A1 | 3/2005 | Thiam et al. | |
| 2005/0114910 A1 | 5/2005 | Lone et al. | |
| 2006/0107339 A1 | 5/2006 | Gotch et al. | |
| 2007/0209083 A1 | 9/2007 | Thiam et al. | |

(Continued)

FOREIGN PATENT DOCUMENTS

| | | |
|---|---|---|
| EP | 0437576 B1 | 7/2002 |
| EP | 1878342 A1 | 1/2008 |

(Continued)

OTHER PUBLICATIONS

Abarrategui and Krangel (2006) "Regulation of T cell receptor alpha gene recombination by transcription," Nat. Immunol., 7:1109-1115 and Corrigendum.

Allen et al. (1986) "B2-Microglobulin is not required for Cell surface expression of the murine class I histocompatibility antigen H-2Db or of a truncated H-2Db," PNAS, 83:7447-7451.

Altmann et al. (1995) "The T Cell Response to HLA-DR Transgenic Mice to Human Myelin Basic Protein and other Antigens in the Presence and Absence of Human CD4," J. Exp. Med., 181:867-875.

(Continued)

*Primary Examiner* — Thaian N Ton
(74) *Attorney, Agent, or Firm* — FisherBroyles, LLP; Rita S. Wu; Margarita Zippin

(57) ABSTRACT

The invention provides genetically modified non-human animals that express chimeric human/non-human MHC I and MHC II polypeptides and/or human or humanized β2 microglobulin polypeptide, as well as embryos, cells, and tissues comprising the same. Also provided are constructs for making said genetically modified animals and methods of making the same. Methods of using the genetically modified animals to study various aspects of human immune system are provided.

18 Claims, 11 Drawing Sheets

Specification includes a Sequence Listing.

(56) References Cited

U.S. PATENT DOCUMENTS

| | | | |
|---|---|---|---|
| 2009/0328240 | A1 | 12/2009 | Sing et al. |
| 2010/0011450 | A1 | 1/2010 | Garcia et al. |
| 2010/0138938 | A1 | 6/2010 | Garcia et al. |
| 2011/0067121 | A1 | 3/2011 | Lone et al. |
| 2013/0111617 | A1 | 5/2013 | Macdonald et al. |
| 2013/0185819 | A1 | 7/2013 | Macdonald et al. |
| 2014/0245466 | A1 | 8/2014 | Macdonald et al. |
| 2014/0245467 | A1 | 8/2014 | Macdonald et al. |
| 2015/0245598 | A1 | 9/2015 | Macdonald et al. |
| 2017/0142944 | A1 | 5/2017 | Macdonald et al. |
| 2017/0164590 | A1 | 6/2017 | Macdonald et al. |
| 2017/0273286 | A1 | 9/2017 | Macdonald et al. |

FOREIGN PATENT DOCUMENTS

| | | |
|---|---|---|
| EP | 1878798 A1 | 1/2008 |
| EP | 0950707 B1 | 2/2009 |
| EP | 1017721 B1 | 2/2009 |
| EP | 1409646 B1 | 6/2012 |
| WO | 199101140 A1 | 2/1991 |
| WO | 199211753 A1 | 7/1992 |
| WO | 199305817 A1 | 4/1993 |
| WO | 199503331 A1 | 2/1995 |
| WO | 1997032603 A1 | 9/1997 |
| WO | 1998024893 A2 | 6/1998 |
| WO | 2001027291 A1 | 4/2001 |
| WO | 2002059263 A2 | 8/2002 |
| WO | 2003006639 A1 | 1/2003 |
| WO | 2005004592 A2 | 1/2005 |
| WO | 2008010099 A2 | 1/2008 |
| WO | 2008010100 A2 | 1/2008 |
| WO | 2009114400 A1 | 9/2009 |
| WO | 2011004192 A1 | 1/2011 |
| WO | 2012007951 A1 | 1/2012 |
| WO | 2012039779 A1 | 3/2012 |
| WO | 2013063340 A1 | 5/2013 |
| WO | 2013063346 A1 | 5/2013 |
| WO | 2013063361 A2 | 5/2013 |
| WO | 2014130667 A1 | 8/2014 |
| WO | 2014130671 A1 | 8/2014 |
| WO | 2014164638 A1 | 10/2014 |
| WO | 2014164640 A1 | 10/2014 |
| WO | 2016164492 A2 | 10/2016 |

OTHER PUBLICATIONS

Alvarez et al. (1995) "V(D)J Recombination and Allelic Exclusion of a TCR Beta-Chain Minilocus Occurs in the Absence of a Functional Promoter," J. of Immunol., 155:1191-1202.
Arnold and Hammerling (1991) "MHC Class-1 Transgenic Mice," Annu. Rev. Immunol., 9:297-322.
Auerbach et al. (2000) "Establishment and Chimera Analysis of 129/SvEV- and C57BL/6-Derived Mouse Embryonic Stem Cell Lines, " BioTechniques, 29:1024-1032.
Baker et al. (1996) "Adaptation of TCR Expression Vectors for the Construction of Mouse-Human Chimeric MBP-Specific TCR Transgenes," J. Neurosci. Research, 45:487-491.
Barber and Lechler (1991) "Interactions between the amino-terminal domains of MCH class II molecules have a profound effect on serologic and T cell recognition: an analysis using recombinant HLA-DR/H-2E molecules," J. Immunol., 147:2346-2353.
Barthold (2004) "Genetically altered mice: phenotypes, no phenotypes, and Faux phenotypes," Genetica, 122:75-88.
Basha et al. (2008) "MHC Class I Endosomal and Lysosomal Trafficking Coincides with Exogenous Antigen Loading in Dendritic cells," PLoS One, 3:e3247, 11 pages.
Bassing et al. (2000) Recombination signal sequences restrict chromosomal V(D)J recombination beyond the 12/23 rule, Nature, 405:583-586.
Benmohamed et al. (2000)"Induction of CTL Response by a Minimal Epitope Vaccine in HLA-A*0201/DR1 Transgenic Mice: Dependence on HLA Class II Restricted TH Response," Hum. Immunol., 61:764-779.

Bernabeu et al. (1984) "B2-Microglobulin from serum associates with MHC class I antigens on the surface of cultured cells," Nature, 308:642-645.
Betser-Cohen et al. (2010) "The Association of MHC Class I Proteins with the 2B4 Receptor Inhibits Self-Killing of Human NK cells," J. Immunol., 184:2761-2768.
Bonnet, et al. (2009) "Molecular Genetics at the T-Cell Receptor β Locus: Insights into the Regulation of V(D)J Recombination," V(D)J Recombination, 650:116-132.
Bouffard et al. (1997) "A Physical Map of Human Chromosome 7: An Integrated YAC Contig Map with Average STS Spacing of 79 kb," Genome Research, 7:673-692.
Brevini et al. (2010) "Embryonic Stem Cells in Domestic Animals; No shortcuts to pig embryonic stem cells," Theriogenology, 74:544-550.
Buta et al. (2013) "Reconsidering pluripotency tests: Do we still need teratoma assays?," Stem Cell Res., 11:552-562.
Carstea et al. (2009) "Germline competence of mouse ES and iPS Cell lines: Chimera technologies and genetic background," World Journals of Stem Cells, 1(1):22-29.
Chamberlain et al. (1988)"Tissue-specific and Cell surface expression of human major histocompatibility complex class I heavy (HLA-B7) and light (B2-microglobulin) chain genes in transgenic mice," PNAS, 86:7690-7694.
Chung et al. (1994) "Functional three-domain single-chain T-Cell receptors," PNAS, 91:12654-12658.
Clark et al. (1987) "Peptide and nucleotide sequences of rat CD4 (W3/25) antigen: evidence for derivation from a structure with four immunoglobulin-related domains," PNAS, 84(6):1649-1653.
Connolly et al. (1988) "The Lyt-2 Molecule Recognizes Residues in the Class I alpha3 Domain in Allogeneic Cytotoxic T Cell Responses," J. Exp. Med., 168:325-341.
Cooper et al. (2007) "An Impaired Breeding Phenotype in Mice with a Genetic Deletion of Beta-2 Microglobulin and Diminished MHC Class I Expression: Role in Reproductive Fitness," Biol. Reprod., 77:274-279.
Corbeil et al. (1996) "HIV-induced Apoptosis Requires the CD4 Receptor Cytoplasmic Tail and Is Accelerated by Interaction of CD4 with p56Ick," J. Exp. Med.,183:39-48.
Cosson and Bonifacino (1992) "Role of Transmembrane Domain Interactions in the Assembly of Class II MHC Molecules," Science, 258:659-662.
Crusio et al. (2004) "Flanking Gene and Genetic Background Problems in Genetically Manipulated Mice," Biol. Psychiatry, 56:381-385.
Danner et al. (2011) "Expression of HLA Class II Molecules in Humanized NOD.Rag1KO.IL2RgKO Mice is Critical for Development and Function of Human T and B cells," PLoS One, 6:e19826, 12 pages.
Database entry for NCB I Reference Sequence: NG 001333.2 (Sep. 19, 2006) "Homo sapiens T cell receptor beta locus (TRB) on chromosome 7".
De Bakker et al. (2006) "A high-resolution HLA and SNP haplotype map for disease association studies in the extended human MHC," Nature Genet. Online Supplement, 33 pages.
De Bakker et al. (2006) "A high-resolution HLA and SNP haplotype map for disease association studies in the extended human MHC," Nature Genet., 38:1166-1172.
De Gassart et al. (2008) "MHC class II stabilization at the surface of human dendritic cells is the result of maturation-dependent MARCH I down-regulation," PNAS, 105:3491-3496.
Dennis (2002) "Welfare issues of genetically modified animals," ILAR Journal, 43(2):100-109.
Doetschman (2009) "Influence of Genetic Background on Genetically Engineered Mouse Penotypes," Methods Mol. Biol., 530:423-433.
Dolan et al. (2004) "Invariant Chain and the MHC Class II Cytoplasmic Domains Regulate Localization of MHC Class II Molecules to Lipid Rafts in Tumor Cell-Based Vaccines," J. Immunol., 172:907-914.
Duke (1989) "Self Recognition by T Cell," J. Exp. Med. 170:59-71.

(56) References Cited

OTHER PUBLICATIONS

El Fakhry et al. (2004) "Delineation of the HLA-DR Region and the Residues Involved in the Association with the Cytoskeleton," J. Biol. Chem., 279:18472-18480.
Ellmeier et al. (1998) "Multiple developmental stage-specific enhancers regulate CD8 expression in developing thymocytes and in thymus-independent T cells," Immunity, 9(4):485-496.
Festing et al. (1999) "Revised nomenclature for strain 129 mice," Mamm. Genome, 10:836.
Firat et al. (2002) "Comparative analysis of the CO8+ T Cell repertoires of H-2 class I wild-ype/HLA-2.1 and H-2 class I knockout/HLA-A2.1 transgenic mice," Internal. Immunol., 14:925-934.
Fleischer et al. (1996) Reactivity of Mouse T-Cell Hybridomas Expressing Human Vβ Gene Segments with Staphylococcal and Streptococcal Superantigens, Infection and Immunity, 64(3):997-994.
Fooksman et al. (2009) "Cutting Edge: Phospholidylinositol 4, 5-Bisphosphate Concentration at the APC Side of the Immunological Synapse Is Required for Effector T Cell Function," J. Immunol., 182:5179-5182.
Friese et al., (2008) "Opposing effects of HLA class I molecules in tuning autoreactive CDS+ T cells in multiple scelerosis," Nature Med., 14(11): 1227-1235.
Fugger et al. (1994) "Expression of HLA-DR4 and human CD4 transgenes in mice determines the variable region beta-chain T-Cell repertoire and mediates an HLA-DR-restricted immune response," PNAS, 91:6151-6155.
Fukui et al. (1993) "T-cell repertoire in a stain of transgenic C57BL/6 mice with the HLA-DRA gene on the X-chromosome," Immunogenetics, 37(3):204-211.
Fukui et al. (1997) "Differential requirement of MHC class II molecules expressed on hematopoietic cells for positive selection of CD4+ thymocytes in TCR α β and TCR β transgenic mice," Internal. Immunol., 9(9):1385-1391.
Gao et al. (1997) "Crystal structure of the complex between human CD88alpha-alpha and HLA-A2," Nature, 387:630-634.
Gao et al. (2000) "Molecular interactions of coreceptor CD8 and MHC class 1: the molecular basis for functional coordination with the T-Cell receptor," Immunol. Today, 21 (12):630-636.
Germain et al., (2002) "T-Cell Development and the CD4-CD5 Lineage Decision, Nature Reviews, Immunol.," 2:309-322.
Goldman et al. (2004) "Transgenic animals in medicine: Integration and expression of foreign genes, theoretical and applied aspects," Med. Sci. Monit., 10(11): RA274-285.
Gomez et al. (2010) "Derivation of cat embryonic stem-like cells from in vitro-produced blastocysts on homologous and heterologous feeder cells," Theriogenology, 74:498-515.
Gruda et al. (2007) "Intracellular Cysteine Residues in the Tail of MHC Class I Proteins Are Crucial for Extracellular Recognition by Leukocyte Ig-Like Receptor 1," J. Immunol., 179:3655-3661.
Gur et al. (1997) "Structural Analysis of Class I MHC Molecules: The Cytoplasmic Domain Is Not Required for Cytoskeletal Association, Aggregation and Internalization," Mol. Immunol., 34:125-132.
Güssow et al. (1987) "The Human B2-Microglobulin Gene. Primary Structure and Definition of the Transcriptional Unit," J. Immunol., 139:3132-3138.
Haks et al. (1999) "Cell-fate decisions in early T cell development: regulation by cytokine receptors and the pre-TCR," Immunol., 11:23-37.
Hanna et al. (1994) "Specific expression of the human CD4 gene in mature CD4 + CD8− and immature CD4+ and CD8+ T cells and in macrophages of transgenic mice," Mol. Cellular Biol., 14(2):1084-1094.
Harton et al. (2016) "Immunological Functions of the Membrane Proximal Region of MHC Class II Molecules," F1000Research, 5:1-12, doi: 10.12688/f1000research.7610.1.
Holdsworth et al. (2009) "The HLA dictionary 2008: a summary of HLA-A, -B, -C-DRB1/3/4/5, and -DQB1 alleles and their association with serologically defined HLA-A, -B, -C, DR, and -DQ antigens," Tissue Antigens, 73:95-170.
Hong et al. (2012) "Derivation and Characterization of Embryonic Stem Cells Lines Derived from Transgenic Fischer 344 and Dark Agouti Rats," Stem Cells and Development, 21(9):1571-1586.
Hostert et al. (1997) "A CD8 genomic fragment that directs subset-specific expression of CD8 in transgenic mice," J. Immunol., 158(9):4270-4281.
Hou et al. (2016) "Derivation of Porcine Embryonic Stem-Like Cells from In Vitro-Produced Blastocyst-Stage Embryos," Scientific Research, 6:1-13.
Houdebine, et al (2002) "The methods to generate transgenic animals and to control transgene expression," J. of Biotech., 98:145-160.
Houdebine, et al (2007) "Methods in Molecular," Biology, 360:163-202.
Huang et al. (1997) "Analysis of the contact sites on the CD4 Molecule with Class II MHC Molecule," J. Immunol., 158:215-225.
Intarapat and Stern (2013) "Chick stem cells: Current progress and future prospects," Stem Cell Res., 11:1378-1392.
International MHC and Autoimmunity Genetics Network (IMAGEN) (2009) "Mapping of multiple 40 susceptibility variants within the MHC region for 7 immune-mediated diseases," PNAS, 1 06: 18680-18685.
Irie et al. (1998) "The cytoplasmic domain of CD8 beta regulates Lck kinase activation and CD8 T cell development," J. Immunol., 161(1):183-191.
Irwin et al. (1989) "Species-restricted interactions between COB an the alpha3 domain of class I influence the magnitude of the xenogeneic response," J. Exp. Med., 170:1091-1101.
Ishimoto et al. (1997) "In vitro and in vivo evidence for high frequency of I-Ab-reactive CD4+ t cells in HLA-DQ or HLA-DRA transgenic mice lacking endogenous MHC class I and/or class II expression," J. Immunol., 159(8):3717-3722.
Itano et al. (1996) "The Cytoplasmic Domain of CD4 Promotes the Development of CD4 Lineage T Cells," J. Exp. Med., 183(3):731-741.
Ito et al. (1996) "HLA-DR4-IE Chimeric Class II Transgenic, Murine Class 11-Deficient Mice Are Susceptible to Experimental Allergic Encephalomyelitis," J. Exp. Med., 183:2635-2644.
Jakobovits (1994) "Humanizing the mouse genome," Cur. Biol., 4(8):761-763.
Jean et al. (2013) "Pluripotent genes in avian stem cells," Develop. Growth Differ., 55:41-51.
Johansson et al. (2005) "Natural killer Cell education in mice with single or multiple major histocompatibility complex class I molecules," J. Exp. Med., 201:1145-1155.
Josson et al. (2011) "B2 microglobulin induces epithelial to mesenchymal transition and confers cancer lethality and bone metastasis in human cancer cells," Cancer Res., 71:1-11.
Kalinke et al. (1990) "Strong Xenogeneic HLA Response in Transgenic Mice after Introducing an Alpha3 Domain into HLA B27," Nature, 348:642-644.
Kaplan et al. (2005) "A new murine tumor model for studying HLA-A2-restricted anti-tumor immunity," Cancer Letters, 224:153-166.
Khor et al. (2002) "Allelic exclusion at the TCRβ locus," Curr. Opin. Immunol., 14:230-234.
Kievits et al. (1987) "HLA-restricted recognition of viral antigens in HLA transgenic mice," Nature 329:447-449.
Killeen et al. (1993) "Regulated expression of human CD4 rescues helper T cell development in mice lacking expression of endogenous CD4," EMBO J., 12(4): 1547-1553.
Kioussis et al. (2002) "Chromatin and CD4, CD8A and CD8B gene expression during thymic differentiation," Nature Rev. Immunol., 2(12):909-919.
Kirwan et al. (2005) "Killer Cell Ig-Like Receptor-Dependent Signaling by Ig-Like Transcript 2 (ILT2/CD85j/LILRB1/ LIR-1)," J. Immunol., 175:5006-5015.
Koller and Orr (1985) "Cloning and complete sequence of an HLA-A2 gene: Analysis of two HLA-A Alleles at the nucleotide Level" J. Immunol. 134(4):2727-2733.

(56) References Cited

OTHER PUBLICATIONS

Koller et al. (1990) "Normal Development of Mice Deficient in B2M, MHC Class I Proteins, and CD8+ T cells," Science, 248:1227-1230.
Koop et al., (1994) "The human T-cell receptor TCRAC/TCRDC (C alpha/C delta) region: organization, sequence, and evolution of 97.6 kb of DNA," Genomics 19(3):478-493.
Krangel et al. (1998) "Development regulation of V(D)J recombination at the TCR α/δ locus," Immunol. Rev., 165:131-147.
Kruisbeek et al., (2000) "Branching out to gain control: how the pre-TCR is linked to multiple functions," Rev. Immunol. Today, 21 (12):637-644.
Kumanovics et al. (2003) "Genomic Organization of the Mammalian MHC," Annu. Rev. Immunol., 21:629-657.
Laface et al. (1995) "Human CD8 Transgene Regulation of HLA Recognition by Murine T cells," J. Exp. Med., 182:1315-1325.
Landau et al. (1988) "The envelope glycoprotein of the human immunodeficiency virus binds to the immunoQiobulin-like domain of CD4," Nature, 334(6178): 159-162.
Laub et al. (2000) "A multiple transgenic mouse model with a partially humanized activation pathway for helper T cell responses," J. Immunol. Methods, 246(1-2):37-50.
Lauzurica P. and Krangel M.S. (1994) "Enhancer-dependent and -independent Steps in the Rearrangement of a Human T Cell Receptor Delta Transgene," J. Exp. Med., 179:43-55.
Law et al. (1994) "Human CD4 Restores Normal T Cell Development and Function in Mice Deficient in Murine CD4," J. Exp. Med., 179(4): 1233-1242.
Leahy (1995) "A structural view of CD4 and CD8," FASEB J., 9:17-25.
Leduc et al. (2000) "T Cell Development in TCRB Enhancer-Deleted Mice: Implications for αβ T Cell Lineage Commitment and Differentiation," J. Immunol., 165:1364-1373.
Lee et al. (1982) "Sequence of an HLA-DR alpha-chain cDNA clone and intron-exon organization of the corresponding gene," Nature, 299:750-752.
Li et al. (2009) "Mamu-A*01/Kb transgenic and MHC Class I knockout mice as a tool for HIV vaccine development," Virology, 387:16-28.
Li et al. (2010) "Transgenic mice with a diverse human T Cell antigen receptor repertoire," Nature Med., 16(9):1029-1034, doi:10.1038/nm.2197.
Li et al. (2013) "Generation of transgenic mice with megabase-sized human yeast artificial chromosomes by yeast spheroplast-embryonic stem cell fusion," Nat. Protoc., 8(8):1567-1582, doi:10.1038/nprot.2013.093.
Lie and Petropoulos (1998) "Advances in quantitative PCR technology: 5' nuclease assays," Curr. Opin. Biotech., 9:43-48.
Linnenbach et al. (1980) "DNA-transformed murine teratocarcinoma cells: regulation of expression of simian virus 40 tumor antigen in stem versus differentiated cells," PNAS, 77(8):4875-4879.
Littman (1987) "The Structure of the CD4 and CD8 Genes," Annual Review of Immunology, 5:561-584.
Lizee et al. (2003) "Control of dendritic cell cross-presentation by the major histocompatibility complex class I cytoplasmic domain," Nature Immunol., 4:1065-1073.
Lynch et al. (2009) "Novel MHC Class I Structures on Exosomes," J. Immunol., 183:1884-1891.
Maddon et al. (1987) "Structure and expression of the human and mouse T4 genes," PNAS, 84(24):9155-9159.
Madsen et al. (1999) "A humanized model for multiple sclerosis using HLA-DR2 and a human T-cell receptor," Nature Genet., 23:343-347.
Maksimenko et al. (2013) "Use of Transgenic Animals in Biotechnology: Prospects and Problems," ACTNA Naturae, 5(1):33-46.
Manz et al. (2009) "Renaissance for mouse models of human hematopoiesis and immunobiology," Nature Immunology, 10(10):1039-1042.
Marsh et al. (2010) "Nomenclature for factors of the HLA system," 2010, Tissue Antigens, 75:291-455.
Marten et al. (2003) "Transgenic mouse methods and protocols," Methods in Molecular Biology, 209:51-58.
Mendez et al. (1997) "Functional transplant of megabase human immunoglobulin loci recapitulates human antibody response in mice," Nature Genet., 15(2):146-156.
Moir et al. (1996) "Postbinding events mediated by human immunodeficiency virus type 1 are sensitive to modifications in the D4-transmembrane linker region of CD4," J. Virology, 70(11):8019-8028.
Moldovan et al. (2002) "CD4 Dimers Constitute the Functional Component Required forT Cell Activation," J. Immunol., 169:6261-6268.
Mombaerts P. et al. (1991) "Creation of a large genomic deletion at the T-cell antigen receptor β-subunit locus in mouse embryonic stem cells by gene targeting," PNAS, 88:3084-3087.
Mombaerts et al. (1992) "Mutations in T-cell antigen receptor genes a and B block thymocyte development at different stages," Nature, 360:225-231.
Mombaerts et al. (1993) "Spontaneous Development of Inflammatory Bowel Disease in T Cell Receptor Mutant Mice," Cell, 75:275-282.
Munoz et al. (2008) "Technical note; Conventional pluripotency markers are unspecific for bovine embryonic-derived cell-lines," Theriogenology, 69:1159-1164.
Murphy et al. (2008) "Janeway's Immunobiology" 7th ed., Garland Science, pp. 125-13B and 196-213.
Musser G. (Encyclopedia Britannica, May 31, 2016) Rodent, Mammal, http://www.britannica.com/animal/rodent.
Nakayama et al. (1989) "Structure and expression of the gene encoding CD8α chain (Leu-2/T8)," Immunogenetics, 30:393-397.
Nakayama et al. (1992) "Recent Duplication of the Two Human CD8 β-chain genes," J. Immunol., 148:1919-1927.
Nickerson et al. (1990) "Expression of HLA-B27 in Transgenic Mice Is Dependent on the Mouse H-20 Genes," J. Exp. Med., 172:1255-1261.
Noordzij et al. (2000) "N-terminal truncated human RAG1 proteins can direct T-cell receptor but not immunogiobulin gene rearrangements," Blood, 96(1):203-209.
Norment et al. (1988) "A second subunit of CD8 is expressed in human T cells," EMBO J., 7(11):3433-3439.
Norment et al. (1989) "Alternatively Spliced mRNA Encodes a Secreted Form of Human CD8α, Characterization of the Human CD8α gene," J. Immunol., 142:3312-3319.
Ostrand-Rosenberg et al. (1991) "Abrogation of Tumorigenicity by MHC Class II Antigen Expression Requires the Cytoplasmic Domain of the Class II Molecule," J. Immunol., 147:2419-2422.
Pajot et al. (2004) "A mouse model of human adaptive immune functions: HLA-A2.1/HLA-DR1-trasngenic H-2 class 1-/class 11-knockout mice," Eur. J. Immunol., 34:3060-3069.
Paris and Stout (2010) "Embryonic Stem Cells in Domestic Animals; Equine embryos and ebryonic stem cells: Defining reliable markers of pluripotency," Theriogenology, 74:516-524.
Pasare et al. (2001) "T cells in mice expressing a transgenic human TCRβ chain get positively selected but cannot be activated in the periphery by signaling through TCR," Intl. Immunol., 13(1):53-62.
Pascolo, et al. (1997) "HLA-A2.1-restricted Education and Cytolytic Activity of CD8+ T Lymphocytes from from β2 Microglobulin (β2m) HLA-A2.1 Monochain Transgenic H-2Db β2m Double Knockout Mice," J. Exp. Med., 185:2043-2051.
Pascolo, et al. (2005) "HLA class I transgenic mice: development, utilisation and improvement," Expert Opinion Biol. Ther., 5(7):919-938.
Perarnau et al. (1988) "Human B2-microglobulin specifically enhances cell-surface expression of HLA class I molecules in transfected murine cells," J. Immunol., 141:1383-1389.
Pettersen et al. (1998) "The TCR-Binding Region of the HLA Class I α2 Domain Signals Rapid Fast Independent Cell, Death: A Direct Pathway for T Cell-Mediated Killing of Target cells," J. Immunol., 160:4343-4352.
Pittet et al. (2003) "Alpha3 Domain Mutants of Peptide/MHC Class I Multimers Allow the Selective Isolation of High Avidity Tumor-Reactive CD8 T cells," J. Immunol., 171:1844-1849.

(56) References Cited

OTHER PUBLICATIONS

Potter et al. (1989) "Substitution at residue 227 of H-2 class I molecules abrogates recognition by CD8-dependent, but not CD8-independent, cytotoxic T lymphocytes," Nature, 337:73-75.
Poueymirou et al. (2007) "F0 generation mice fully derived from gene-targeted embryonic stem cells allowing immediate phenotypic analyses," Nature Biotech., 25:91-99.
Quinn et al. (1997) "Virus-Specific, CD8+ Major Histocompatibility Complex Class 1-Restricted Cytotoxic T Lymphocytes in Lymphocytic Choriomeningitis Virus-Infected B2-Microglobulin-Deficient Mice," J. Virol., 71 :8392-8396.
Rack et al. (1997) "A Chromosome 14q11/TCRα/δ Specific Yeast Artificial Chromosome Improves the Detection Rate and Characterization of Chromosome Abnormalities in T-Lymphoproliferative Disorders," Blood, 90(3):1233-1240.
Raffegerst et al. (2009) "Diverse Hematological Malignancies Including Hodgkin-Like Lymphomas Develop in Chimeric MHC Class II Transgenic Mice," PLoS One, 4:e8539, 12 pages.
Reipert et al. (2009) "Opportunities and limitations of mouse models humanized for HLA class II antigens," Thrombosis and Haemostasis, 7(Suppl. 1):92-97.
Ren et al. (2006) "Construction of bioactive chimeric MHC class I tetramer by expression and purification of human-murine chimeric MHC heavy chain and β2M as a fusion protein in *Escherichia coli*," Protein Expression and Purification, 50:171-78.
Rodriguez-Cruz et al. (2011) "Natural Splice Variant of MHC Class I Cytoplasmic Tail Enhances Dendritic Cell-Induced CD8+ T-Cell Responses and Boosts Anti-Tumor Immunity," PLoS One, 6:e22939, 10 pages.
Rohrlich et al. (2003) "HLA-B*0702 transgenic, H-2K$^b$D$^b$ doubleknockout mice: phenotypical and functional characterization in response to influenza virus," International Immunology, 15(6):765-772.
Rosano et al. (2005) "The three-dimensional structure of B2 microglobulin: Results from X-ray crystallography," Biochim. Biophys. Acta, 1753:85-91.
Rothe et al. (1993) Functional expression of a human TCRβ gene in transgenic mice, Intl. Immunol., 5(1):11-17.
Rowen et al., (1996) "The Complete 685-Kilobase DNA Sequence of the Human β T Cell Receptor Locus," Science, 272:1755-1762.
Rubio et al. (2004) "Cross-linking of MHC class I molecules on human NK cells inhibits NK cell function, segregates MHC I from the NK cell synapse, and induces intracellular phosphotyrosines," J. Leukoc. Biol., 76:116-124.
Salter et al. (1989) "Polymorphism in the alpha3 domain of HLA-A molecules affects binding to CD8," Nature, 338:345-347.
Salter et al. (1990) "A binding site for the T-cell co-receptor CD8 on the alpha 3 domain of HLA-A2," Nature, 345:41-46.
Samberg et al. (1989) "The α3 domain of major histocompatibility complex class I molecules plays a critical role in cytotoxic T lymphocyte stimulation," Eur. J. Immunol., 19(12):2349-2354.
Sanders et al. (1991) "Mutations in CD8 that Affect Interactions with HLA Class I and Monoclonal Anti-CD8 Antibodies," J. Exp. Med., 174:371-379.
Santagata et al. (2000) "The genetic and biochemical basis of Omenn syndrome," Immunological Reviews, 178:64-74.
Scheer et al. (2013) "Generation and utility of genetically humanized mouse models." Drug Discovery Today, 18(23/24):1200-1211.
Schwarz et al. (1996) "RAG mutations in human B cell negative SCID," Science, 274(5284):97-99.
Sebzda et al. (1999) "Selection of the T Cell Repertoire," Annu. Rev. Immunol., 17:829-874.
Shankarkumar (2004) "The Human Leukocyte Antigen (HLA) System," Int. J. Hum. Genet., 4:91-103.
Sherman et al. (1992) "Selecting T Cell Receptors with High Affinity for Self-MHC by Decreasing the Contribution of CD8," Science, 258:815-818.
Shin et al. (2006) "Surface expression of MHC class II in dendritic cells is controlled by regulated ubiquitination," Nature, 444:115-118.

Shinkai et al. (1992) "RAG-2-deficient mice lack mature lymphocytes owing to inability to initiate V(D)J rearrangement," Cell 68(5):855-67.
Shinohara et al. (2007) "Active integration: new strategies for transgenesis," Transgenic Res., 16:333-339.
Shiroishi et al. (2003) "Human inhibitory receptors Ig-like transcript 2 (ILT2) and ILT4 compete with CD8 for MHC class I binding and bind preferentially to HLA-G," PNAS, 100:8856-8861.
Shultz et al. (2007) "Humanized mice in translational biomedical research," Nature Rev., 7:118-130.
Sigmund (2000) "Viewpoint: Are Studies in Genetically Altered Mice Out of Control?," Arterioscler. Thromb. Vasc. Biol., p. 1425-1429.
Sims et al (2004) "Genetic Susceptibility to Ankylosing Spondylitis," Cur. Mol. Med., 4(1):13-20.
Singer et al. (2008) "Lineage fate and intense debate: myths, models and mechanisms of CD4/CDS lineage choice," Nature Rev. Immunol., 8(10):788-801.
Siu et al. (1994) "A transcriptional silencer controls the developmental expression of the CD4 gene," EMBO J., 13(15):3570-3579.
Sleckman et al. (2000) "Mechanisms that direct ordered assembly of T cell receptor β locus V, D, and J gene segments," PNAS, 97(14):7975-7980.
Smiley et al. (1995) "Transgenic mice expressing MHC class II molecules with truncated A-beta cytoplasmic domains reveal signaling-independent defects in antigen presentation," Internal. Immunol., 7:665-677.
Smiley et al. (1996) "Truncation of the class II beta-chain cytoplasmic domain influences the level of class II/invariant chain-derived peptide complexes," PNAS, 93:241-244.
Street et al. (2002) "Limitations of HLA-transgenic mice in presentation of HLA-restricted cytotoxic T-cell epitopes from endogenously processed human papillomavirus type 16 E7 protein," Immunology, 106:526-536.
Takaki et al. (2006) "HLA-A*0201-Restricted T cells from Humanized NOD Mice Recognize Autoantigens of Potential Clinical Relevance to Type I Diabetes," J. Immunol., 176:3257-3265.
Tanabe et al. (1989) "Analysis of xenoantigenicity of HLA Class I molecules by a complete series of human-mouse hybrid genes," Transplantation, 48:1, 135-140.
Taneja and David (1998) "HLA Transgenic Mice as Humanized Mouse Models of Disease and Immunity," J. Clin. Invest., 101:921-926.
Taneja and David (2009) "Spontaneous autoimmune myocarditis and cardiomyopathy in HLA-DQ8.NODAbo transgenic mice," Journal of Autoimmunity 33:260-269.
Taylor et al. (1993) "Human immunoglobulin transgenes undergo rearrangement, somatic mutation and class switching in mice that lack endogenous IgM," Int. Immunol., 6(4):579-591.
Theobald et al. (1995) "Targeting p53 as a general tumor antigen," PNAS, 92:11993-11997.
Tishon et al. (2000) "Transgenic Mice Expressing Human HLA and CD8 Molecules Generate HLA-Restricted Measles Virus Cytotoxic T Lymphocytes of the Same Specificity as Humans with Natural Measles Infection," Virology, 275:286-293.
Tong et al. (2010) "Production of p53 gene knockout rats by homologous recombination in embryonic stem cells," Nature Letters, 467:211-215.
Toyonaga et al. (1985) "Organization and sequences of the diversity, joining, and constant region genes of the human T-cell receptor beta chain," PNAS. 82(24):8624-8628.
Ureta-Vidal et al. (1999) "Phenotypical and Functional Characterization of the CD8 + T Cell Repertoire of HLA-A2.1 Transgenic, H-2Kb°Db° Double Knockout Mice," J. Immunol., 163:2555-2560.
Valenzuela et al. (2003) "High-throughput engineering of the mouse genome coupled with high-resolution expression analysis", Nature Biotech., 21:652-659.
Vignali et al. (1992) "Species-specific Binding of CD4 to the Beta2 Domain of Major Histocompatibility Complex Class II Molecules," J. Exp. Med., 175:925-932.
Vignali et al. (1996) "The Two Membrane Proximal Domains of CD4 Interact with the T Cell Receptor," J. Exp. Med., 183:2097-2107.

(56) References Cited

OTHER PUBLICATIONS

Villa et al. (1998) "Partial V(D)J recombination activity leads to Omenn syndrome," Cell 93(5): 855-896.
Villa et al. (1999) "Omenn syndrome: a disorder of Rag1 and Rag2 genes," J. Clin. Immunol., 19(2):87-97.
Viney et al. (1992) "Generation of Monoclonal Antibodies Against a Human T Cell Receptor β chain Expressed in Transgenic Mice," Hybridoma, 11(6):701-714.
Vitiello et al. (1991) "Analysis of the HLA-restricted Influenza-specific Cytotoxic T Lymphocyte Response in 6 Transgenic Mice Carrying a Chimeric Human-Mouse Class I Major Histocompatibility Complex," J. Exp. Med., 173:1007-1015.
Vollmer et al. (2000) "Antigen contacts by Ni-reactive TCR: typical αβ chain cooperation versus a chain-dominated specificity," IntL. Immunol.,12(12):1723-1731.
Vugmeyster et al. (1998) "Major histocompatibility complex (MHC) class I KbDb –/– deficient mice possess functional CD8 + T cells and natural killer cells," PNAS, 95:12492-12497.
Wagner et al. (1994) "Antibodies generated from human immunoglobulin miniloci in transgenic mice," Nucleic Acids Res., 22(8):1389-1393.
Wagner et al. (1994) "Ligation of MHC Class I and Class II Molecules Can Lead to Heterologous Desensitization of Signal Transduction Pathways That Regulate Homotypic Adhesion in Human Lymphocytes," J. Immunol., 152:5275-5287.
Wagner et al. (1994) "The diversity of antigen-specific monoclonal antibodies from transgenic mice bearing human immunogiobulin gene miniloci," Eur. J. Immunol., 24(11):2672-2681.
Wang and Reinherz (2001) "Structural basis of T cell recognition of peptides bound to MHC molecules," Mol. Immunol., 38:1039-1049.
Wei et al. (1996) "Repertoire and Organization of Human T-Cell Receptor a Region Variable Genes," Short Communication, Genomics, 38:442-445.
Wen et al. (1998) "Induction of Insulitis by Glutamic Acid Decarboxylase Peptide-specific and HLA-DQ8-restricted CD4+ T Cells from Human DQ Transgenic Mice," J. Clin. Invest., 102(5):947-957.
Willcox et al. (2003) "Crystal structure of HLA-A2 bound to LIR-1, a host and viral major histocompatibility complex receptor," Nature Immunol., 4:913-919.
Wong and Wen (2004) "What can the HLA transgenic mouse tell us about autoimmune diabetes?," Diabetologia, 47:1476-1487.
Woodle et al. (1997) "Anti-Human Class I MHC Antibodies Induce Apoptosis by a Pathway That Is Distinct from the Fas Antigen-Meidaled Pathway," J. Immunol., 158:2156-2164.
Woods et al. (1994) "Human Major Histocompatibility Complex Class 11-Restricted T Cell, Responses in Transgenic Mice," J. Exp. Med., 180:173-181.
Wooldridge et al. (2010) "MHC Class I Molecules with Superenhanced CD8 Binding Properties Bypass the Requirement for Cognate TCR Recognition and Nonspecifically Activate CTLs," J. Immunol., 184:3357-3366.
Wu et al. (1997) "Dimeric association and segmental variability in the structure of human CD4," Nature, 387:527.
Yamamoto et al. (1994) "Functional Interaction between Human Histocompatibility Leukocyte Antigen (HLA) Class 27 II and Mouse CD4 Molecule in Antigen Recognition by T cells in HLA-DR and DQ Transgenic Mice," J. Exp. Med., 180:165-171.
Yoshikai et al. (1985) "Organization and sequences of the variable, joining and constant region genes of the human T-cell receptor alpha-chain," Nature, 316(6031):837-840.
Zamoyska (1998) "CD4 and CDS: modulators of T cell receptor recognition of antigen and of immune responses?," Curr. Opin. Immunol., 10:82-87.
Zhou et al., (2009) "Developing tTA transgenic rats for inducible and reversible gene expression," International Journal of Biological Sciences, 5:171-181.
Zijlstra et al. (1990) "B2-Microglobulin deficient mice lack CD4-8+ cytolytic T Cells," Nature, 344:742-746.
Zumla et al. (1992) "Co-expression of human T cell receptor chains with mouse CD3 on the cell surface of a mouse T cell hybridoma," J. Immunol. Methods., 149(1):69-76.
Zumla et al. (1992) "Use of a murine T-cell hybridoma expressing human T-cell receptor alpha-and betagene products as a tool for the production of human T-cell receptor-specific monoclonal antibodies," Human Immunol., 35(3):141-148.
International Search Report and Written Opinion for PCT/US2014/023076, dated Jul. 18, 2014.
International Search Report and Written Opinion for PCT/US2012/062042, dated Feb. 18, 2013.
International Search Report and Written Opinion for PCT/US2012/062029, dated Feb. 28, 2013.
International Search Report and Written Opinion for PCT/US2014/023068, dated Jul. 24, 2014.
International Search Report and Written Opinion for PCT/US2014/017395, dated Jun. 2, 2014.
International Search Report and Written Opinion for PCT/US2014/017387, dated Jun. 2, 2014.
International Search Report and Written Opinion for PCT/US2016/026260, dated Aug. 11, 2016.
Extended European Search Report with respect to Europe Application No. 17184955.7, dated Nov. 24, 2017.
Non-Final Office Action with Respect to U.S. Appl. No. 14/185,316, dated Dec. 17, 2015.
Non-Final Office Action with Respect to U.S. Appl. No. 14/185,301 dated Jun. 16, 2016.
Final Office Action with Respect to U.S. Appl. No. 14/185,301 dated Jan. 8, 2016.
English Translation of Office Action with Respect to Japan Application No. 2014-539027 dated Sep. 6, 2016.
Statement of Relatedness under MPEP 2001.06 with Respect to U.S. Appl. No. 15/839,655 dated May 2, 2018.

SEQUENCE LISTING

<160> NUMBER OF SEQ ID NOS: 45

<210> SEQ ID NO 1
<211> LENGTH: 19
<212> TYPE: DNA
<213> ORGANISM: Artificial Sequence
<220> FEATURE:
<223> OTHER INFORMATION: synthetic

```
<400> SEQUENCE: 1
cagaacgcca ggctgtaac                                                 19

<210> SEQ ID NO 2
<211> LENGTH: 20
<212> TYPE: DNA
<213> ORGANISM: Artificial Sequence
<220> FEATURE:
<223> OTHER INFORMATION: synthetic

<400> SEQUENCE: 2
ggagagcagg gtcagtcaac                                                20

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3
caccgccact cacagctcct taca                                           24

<210> SEQ ID NO 4
<211> LENGTH: 22
<212> TYPE: DNA
<213> ORGANISM: Artificial Sequence
<220> FEATURE:
<223> OTHER INFORMATION: synthetic

<400> SEQUENCE: 4
gtgggcacca tcttcatcat tc                                             22

<210> SEQ ID NO 5
<211> LENGTH: 22
<212> TYPE: DNA
<213> ORGANISM: Artificial Sequence
<220> FEATURE:
<223> OTHER INFORMATION: synthetic

<400> SEQUENCE: 5
cttcctttcc agggtgtgac tc                                             22

<210> SEQ ID NO 6
<211> LENGTH: 23
<212> TYPE: DNA
<213> ORGANISM: Artificial Sequence
<220> FEATURE:
<223> OTHER INFORMATION: synthetic

<400> SEQUENCE: 6
aggcctgcga tcaggtggca cct                                            23

<210> SEQ ID NO 7
<211> LENGTH: 19
<212> TYPE: DNA
<213> ORGANISM: Artificial Sequence
<220> FEATURE:
<223> OTHER INFORMATION: synthetic

<400> SEQUENCE: 7
ggtggagagg ctattcggc                                                 19

<210> SEQ ID NO 8
<211> LENGTH: 17
```

```
<212> TYPE: DNA
<213> ORGANISM: Artificial Sequence
<220> FEATURE:
<223> OTHER INFORMATION: synthetic

<400> SEQUENCE: 8
gaacacggcg gcatcag                                                      17

<210> SEQ ID NO 9
<211> LENGTH: 23
<212> TYPE: DNA
<213> ORGANISM: Artificial Sequence
<220> FEATURE:
<223> OTHER INFORMATION: synthetic

<400> SEQUENCE: 9
tgggcacaac agacaatcgg ctg                                               23

<210> SEQ ID NO 10
<211> LENGTH: 140
<212> TYPE: DNA
<213> ORGANISM: Artificial Sequence
<220> FEATURE:
<223> OTHER INFORMATION: synthetic

<400> SEQUENCE: 10
tttgtaaaca aagtctaccc agagacagat gacagacttc agctccaatg ctgattggtt       60
cctcacttgg gaccaaccct accggtataa cttcgtataa ggtatcctat acgaagttat      120
atgcatggcc tccgcgccgg                                                  140

<210> SEQ ID NO 11
<211> LENGTH: 140
<212> TYPE: DNA
<213> ORGANISM: Artificial Sequence
<220> FEATURE:
<223> OTHER INFORMATION: synthetic

<400> SEQUENCE: 11
cgacctgcag ccggcgcgcc ataacttcgt ataaggtatc ctatacgaag ttatctcgag       60
cacaggcatt tgggtgggca gggatggacg gtgactggga caatcgggat ggaagagcat      120
agaatgggag ttagggaaga                                                  140

<210> SEQ ID NO 12
<211> LENGTH: 17
<212> TYPE: DNA
<213> ORGANISM: Artificial Sequence
<220> FEATURE:
<223> OTHER INFORMATION: synthetic

<400> SEQUENCE: 12
cgaggagccc cggtaca                                                      17

<210> SEQ ID NO 13
<211> LENGTH: 20
<212> TYPE: DNA
<213> ORGANISM: Artificial Sequence
<220> FEATURE:
<223> OTHER INFORMATION: synthetic

<400> SEQUENCE: 13
aagcgcacga actccttgtt                                                   20

<210> SEQ ID NO 14
```

```
<211> LENGTH: 17
<212> TYPE: DNA
<213> ORGANISM: Artificial Sequence
<220> FEATURE:
<223> OTHER INFORMATION: synthetic

<400> SEQUENCE: 14
ctctgtcggc tatgtgg                                                     17

<210> SEQ ID NO 15
<211> LENGTH: 22
<212> TYPE: DNA
<213> ORGANISM: Artificial Sequence
<220> FEATURE:
<223> OTHER INFORMATION: synthetic

<400> SEQUENCE: 15
ggactcccag aatctcctga ga                                               22

<210> SEQ ID NO 16
<211> LENGTH: 25
<212> TYPE: DNA
<213> ORGANISM: Artificial Sequence
<220> FEATURE:
<223> OTHER INFORMATION: synthetic

<400> SEQUENCE: 16
gagtcatgaa ccatcactgt gaaga                                            25

<210> SEQ ID NO 17
<211> LENGTH: 16
<212> TYPE: DNA
<213> ORGANISM: Artificial Sequence
<220> FEATURE:
<223> OTHER INFORMATION: synthetic

<400> SEQUENCE: 17
tggtgggttg ctggaa                                                      16

<210> SEQ ID NO 18
<211> LENGTH: 90
<212> TYPE: DNA
<213> ORGANISM: Artificial Sequence
<220> FEATURE:
<223> OTHER INFORMATION: synthetic

<400> SEQUENCE: 18
ctgtttcttc cctaactccc attctatgct cttccatccc gaccgcggcc caatctctct      60
ccactacttc ctgcctacat gtatgtaggt                                       90

<210> SEQ ID NO 19
<211> LENGTH: 80
<212> TYPE: DNA
<213> ORGANISM: Artificial Sequence
<220> FEATURE:
<223> OTHER INFORMATION: synthetic

<400> SEQUENCE: 19
caaggtttcc tcctatgatg cttgtgtgaa actcggggcc ggccagcatt taacagtaca      60
gggatgggag cacagctcac                                                  80

<210> SEQ ID NO 20
<211> LENGTH: 80
<212> TYPE: DNA
<213> ORGANISM: Artificial Sequence
```

```
<220> FEATURE:
<223> OTHER INFORMATION: synthetic

<400> SEQUENCE: 20
gaaagcagtc ttcccagcct tcacactcag aggtacaaat ccccattttc atattagcga    60
ttttaattta ttctagcctc                                                80

<210> SEQ ID NO 21
<211> LENGTH: 80
<212> TYPE: DNA
<213> ORGANISM: Artificial Sequence
<220> FEATURE:
<223> OTHER INFORMATION: synthetic

<400> SEQUENCE: 21
tcttccctaa ctcccattct atgctcttcc atcccgaccg cggcccaatc tctctccact    60
acttcctgcc tacatgtatg                                                80

<210> SEQ ID NO 22
<211> LENGTH: 100
<212> TYPE: DNA
<213> ORGANISM: Artificial Sequence
<220> FEATURE:
<223> OTHER INFORMATION: synthetic

<400> SEQUENCE: 22
gagttcctcc atcacttcac tgggtagcac agctgtaact gtccagcctg tcctgggctg    60
caggtggtgg gcgttgcggg tggggccggt taaggttcca                         100

<210> SEQ ID NO 23
<211> LENGTH: 100
<212> TYPE: DNA
<213> ORGANISM: Artificial Sequence
<220> FEATURE:
<223> OTHER INFORMATION: synthetic

<400> SEQUENCE: 23
tcccacatcc tattttaatt tgctccatgt tctcatctcc atcagcacag ctcgagataa    60
cttcgtataa tgtatgctat acgaagttat atgcatggcc                         100

<210> SEQ ID NO 24
<211> LENGTH: 100
<212> TYPE: DNA
<213> ORGANISM: Artificial Sequence
<220> FEATURE:
<223> OTHER INFORMATION: synthetic

<400> SEQUENCE: 24
atacgaagtt atgctagtaa ctataacggt cctaaggtag cgagtggctt acaggtaggt    60
gcgtgaagct tctacaagca cagttgcccc ctgggaagca                         100

<210> SEQ ID NO 25
<211> LENGTH: 17
<212> TYPE: DNA
<213> ORGANISM: Artificial Sequence
<220> FEATURE:
<223> OTHER INFORMATION: synthetic

<400> SEQUENCE: 25
tgcggccgat cttagcc                                                   17

<210> SEQ ID NO 26
```

```
<210> SEQ ID NO 26
<211> LENGTH: 18
<212> TYPE: DNA
<213> ORGANISM: Artificial Sequence
<220> FEATURE:
<223> OTHER INFORMATION: synthetic

<400> SEQUENCE: 26
ttgaccgatt ccttgcgg                                                 18

<210> SEQ ID NO 27
<211> LENGTH: 21
<212> TYPE: DNA
<213> ORGANISM: Artificial Sequence
<220> FEATURE:
<223> OTHER INFORMATION: synthetic

<400> SEQUENCE: 27
acgagcgggt tcggcccatt c                                             21

<210> SEQ ID NO 28
<211> LENGTH: 18
<212> TYPE: DNA
<213> ORGANISM: Artificial Sequence
<220> FEATURE:
<223> OTHER INFORMATION: synthetic

<400> SEQUENCE: 28
ccccacagca cgtttcct                                                 18

<210> SEQ ID NO 29
<211> LENGTH: 23
<212> TYPE: DNA
<213> ORGANISM: Artificial Sequence
<220> FEATURE:
<223> OTHER INFORMATION: synthetic

<400> SEQUENCE: 29
cgtcccattg aagaaatgac act                                           23

<210> SEQ ID NO 30
<211> LENGTH: 15
<212> TYPE: DNA
<213> ORGANISM: Artificial Sequence
<220> FEATURE:
<223> OTHER INFORMATION: synthetic

<400> SEQUENCE: 30
tggcagccta agagg                                                    15

<210> SEQ ID NO 31
<211> LENGTH: 18
<212> TYPE: DNA
<213> ORGANISM: Artificial Sequence
<220> FEATURE:
<223> OTHER INFORMATION: synthetic

<400> SEQUENCE: 31
ccccacagca cgtttcct                                                 18

<210> SEQ ID NO 32
<211> LENGTH: 17
<212> TYPE: DNA
<213> ORGANISM: Artificial Sequence
<220> FEATURE:
<223> OTHER INFORMATION: synthetic

<400> SEQUENCE: 32
```
acccgctccg tcccatt 17

<210> SEQ ID NO 33
<211> LENGTH: 18
<212> TYPE: DNA
<213> ORGANISM: Artificial Sequence
<220> FEATURE:
<223> OTHER INFORMATION: synthetic

<400> SEQUENCE: 33
agcctaagag ggagtgtc 18

<210> SEQ ID NO 34
<211> LENGTH: 20
<212> TYPE: DNA
<213> ORGANISM: Artificial Sequence
<220> FEATURE:
<223> OTHER INFORMATION: synthetic

<400> SEQUENCE: 34
agaccctggt gatgctggaa 20

<210> SEQ ID NO 35
<211> LENGTH: 18
<212> TYPE: DNA
<213> ORGANISM: Artificial Sequence
<220> FEATURE:
<223> OTHER INFORMATION: synthetic

<400> SEQUENCE: 35
cgcttgggtg ctccactt 18

<210> SEQ ID NO 36
<211> LENGTH: 18
<212> TYPE: DNA
<213> ORGANISM: Artificial Sequence
<220> FEATURE:
<223> OTHER INFORMATION: synthetic

<400> SEQUENCE: 36
tcgaagtgga gaggttta 18

<210> SEQ ID NO 37
<211> LENGTH: 21
<212> TYPE: DNA
<213> ORGANISM: Artificial Sequence
<220> FEATURE:
<223> OTHER INFORMATION: synthetic

<400> SEQUENCE: 37
tggaatggag tgagcagctt t 21

<210> SEQ ID NO 38
<211> LENGTH: 20
<212> TYPE: DNA
<213> ORGANISM: Artificial Sequence
<220> FEATURE:
<223> OTHER INFORMATION: synthetic

<400> SEQUENCE: 38
gcacggtccc cttcttagtg 20

<210> SEQ ID NO 39
<211> LENGTH: 18
<212> TYPE: DNA

```
<213> ORGANISM: Artificial Sequence
<220> FEATURE:
<223> OTHER INFORMATION: synthetic

<400> SEQUENCE: 39
tgacttccta aatttctc                                                   18

<210> SEQ ID NO 40
<211> LENGTH: 21
<212> TYPE: DNA
<213> ORGANISM: Artificial Sequence
<220> FEATURE:
<223> OTHER INFORMATION: synthetic

<400> SEQUENCE: 40
ctggcggctt gaagaatttg g                                               21

<210> SEQ ID NO 41
<211> LENGTH: 24
<212> TYPE: DNA
<213> ORGANISM: Artificial Sequence
<220> FEATURE:
<223> OTHER INFORMATION: synthetic

<400> SEQUENCE: 41
catgatttcc aggttggctt tgtc                                            24

<210> SEQ ID NO 42
<211> LENGTH: 26
<212> TYPE: DNA
<213> ORGANISM: Artificial Sequence
<220> FEATURE:
<223> OTHER INFORMATION: synthetic

<400> SEQUENCE: 42
cgatttgcca gctttgaggc tcaagg                                          26

<210> SEQ ID NO 43
<211> LENGTH: 21
<212> TYPE: DNA
<213> ORGANISM: Artificial Sequence
<220> FEATURE:
<223> OTHER INFORMATION: synthetic

<400> SEQUENCE: 43
cctcacttgg gaccaaccct a                                               21

<210> SEQ ID NO 44
<211> LENGTH: 20
<212> TYPE: DNA
<213> ORGANISM: Artificial Sequence
<220> FEATURE:
<223> OTHER INFORMATION: synthetic

<400> SEQUENCE: 44
ttgtcccagt caccgtccat                                                 20

<210> SEQ ID NO 45
<211> LENGTH: 24
<212> TYPE: DNA
<213> ORGANISM: Artificial Sequence
<220> FEATURE:
<223> OTHER INFORMATION: synthetic
```

```
<400> SEQUENCE: 45
tgcatctcga gcacaggcat ttgg                                              24
```

GENETICALLY MODIFIED MAJOR HISTOCOMPATIBILITY COMPLEX MICE

CROSS REFERENCE TO RELATED APPLICATIONS

This application is a continuation of U.S. application Ser. No. 14/830,464, filed Aug. 19, 2015, which application claims benefit under 35 U.S.C. § 119(e) of U.S. provisional patent application Ser. No. 62/039,333, filed Aug. 19, 2014 and is a continuation-in-part application of U.S. application Ser. No. 14/185,316, filed Feb. 20, 2014, which claims the benefit under 35 § 119(e) of U.S. Provisional Patent Application Ser. No. 61/767,811, filed Feb. 22, 2013, all of which are hereby incorporated by reference in their entirety.

SEQUENCE LISTING

A Sequence Listing in the form of a text file entitled, "2015-08-19-T0036US01-SEQ-LIST_ST25," created on Aug. 19, 2015, (size 9.20 Kb) is incorporated herein by reference in its entirety.

FIELD OF THE INVENTION

The present invention relates to a genetically modified non-human animal, e.g., a rodent (e.g., a mouse or a rat), that expresses a human or humanized Major Histocompatibility Complex (MHC) class I and a human or humanized MHC class II molecules. The invention also relates to a genetically modified non-human animal, e.g., a mouse or a rat, that expresses a human or humanized MHC I protein (e.g., MHC I α chain) and a human or humanized MHC II protein (e.g., MHC II α and MHC II β chains), and further expresses a human or humanized β2 microglobulin; as well as embryos, tissues, and cells expressing the same. The invention further provides methods for making a genetically modified non-human animal that expresses both human or humanized MHC class I and class II proteins, and/or β2 microglobulin. Also provided are methods for identifying and evaluating peptides in the context of a humanized cellular immune system in vitro or in a genetically modified non-human animal, and methods of modifying an MHC locus of a non-human animal, e.g., a mouse or a rat, to express a human or humanized MHC I and a human or humanized MHC II proteins.

BACKGROUND OF THE INVENTION

In the adaptive immune response, foreign antigens are recognized by receptor molecules on B lymphocytes (e.g., immunoglobulins) and T lymphocytes (e.g., T cell receptor or TCR). These foreign antigens are presented on the surface of cells as peptide fragments by specialized proteins, generically referred to as major histocompatibility complex (MHC) molecules. MHC molecules are encoded by multiple loci that are found as a linked cluster of genes that spans about 4 Mb. In mice, the MHC genes are found on chromosome 17, and for historical reasons are referred to as the histocompatibility 2 (H-2) genes. In humans, the genes are found on chromosome 6 and are called human leukocyte antigen (HLA) genes. The loci in mice and humans are polygenic; they include three highly polymorphic classes of MHC genes (class I, II and III) that exhibit similar organization in human and murine genomes (see FIG. 2 and FIG. 3, respectively).

MHC loci exhibit the highest polymorphism in the genome; some genes are represented by >300 alleles (e.g., human HLA-DRβ and human HLA-B). All class I and II MHC genes can present peptide fragments, but each gene expresses a protein with different binding characteristics, reflecting polymorphisms and allelic variants. Any given individual has a unique range of peptide fragments that can be presented on the cell surface to B and T cells in the course of an immune response.

Both humans and mice have class I MHC genes (see FIG. 2 and FIG. 3, respectively). In humans, the classical class I genes are termed HLA-A, HLA-B and HLA-C, whereas in mice they are H-2K, H-2D and H-2L. Class I molecules consist of two chains: a polymorphic α-chain (sometimes referred to as heavy chain) and a smaller chain called β2-microglobulin (also known as light chain), which is generally not polymorphic (FIG. 1, left). These two chains form a non-covalent heterodimer on the cell surface. The α-chain contains three domains (α1, α2 and α3). Exon 1 of the α-chain gene encodes the leader sequence, exons 2 and 3 encode the α1 and α2 domains, exon 4 encodes the α3 domain, exon 5 encodes the transmembrane domain, and exons 6 and 7 encode the cytoplasmic tail. The α-chain forms a peptide-binding cleft involving the α1 and α2 domains (which resemble Ig-like domains) followed by the α3 domain, which is similar to β2-microglobulin.

β2 microglobulin is a non-glycosylated 12 kDa protein; one of its functions is to stabilize the MHC class I α-chain. Unlike the α-chain, the β2 microglobulin does not span the membrane. The human β2 microglobulin locus is on chromosome 15, while the mouse locus is on chromosome 2. The β2 microglobulin gene consists of 4 exons and 3 introns. Circulating forms of β2 microglobulin are present in serum, urine, and other body fluids; non-covalently MHC I-associated β2 microglobulin can be exchanged with circulating β2 microglobulin under physiological conditions.

Class I MHC molecules are expressed on all nucleated cells, including tumor cells. They are expressed specifically on T and B lymphocytes, macrophages, dendritic cells and neutrophils, among other cells, and function to display peptide fragments (typically 8-10 amino acids in length) on the surface to CD8+ cytotoxic T lymphocytes (CTLs). CTLs are specialized to kill any cell that bears an MHC I-bound peptide recognized by its own membrane-bound TCR. When a cell displays peptides derived from cellular proteins not normally present (e.g., of viral, tumor, or other non-self origin), such peptides are recognized by CTLs, which become activated and kill the cell displaying the peptide.

Both humans and mice also have class II MHC genes (see FIGS. 2 and 3, respectively). In humans, the classical MHC II genes are termed HLA-DP, HLA-DQ, and HLA-DR, whereas in mice they are H-2A and H-2E (often abbreviated as I-A and I-E, respectively). Additional proteins encoded by genes in the MHC II locus, HLA-DM and HLA-DO in humans, and H-2M and H-2O in mice, are not found on the cell surface, but reside in the endocytic compartment and ensure proper loading of MHC II molecules with peptides. Class II molecules consist of two polypeptide chains: α chain and β chain. The extracellular portion of the α chain contains two extracellular domains, α1 and α2; and the extracellular portion of the β chain also contains two extracellular domains, β1 and β2 (see FIG. 1, right). The α and the β chains are non-covalently associated with each other.

MHC class II molecules are expressed on antigen-presenting cells (APCs), e.g., B cells, macrophages, dendritic cells, endothelial cells during a course of inflammation, etc. MHC II molecules expressed on the surface of APCs typically present antigens generated in intracellular vesicles to CD4+ T cells. In order to participate in CD4+ T cell engagement, the MHC class II complex with the antigen of interest must be sufficiently stable to survive long enough to engage a CD4+ T cell. When a CD4+ T helper cell is engaged by a foreign peptide/MHC II complex on the surface of APC, the T cell is activated to release cytokines that assist in immune response to the invader.

Not all antigens will provoke T cell activation due to tolerance mechanisms. However, in some diseases (e.g., cancer, autoimmune diseases) peptides derived from self-proteins become the target of the cellular component of the immune system, which results in destruction of cells presenting such peptides. There has been significant advancement in recognizing antigens that are clinically significant (e.g., antigens associated with various types of cancer). However, in order to improve identification and selection of peptides that will provoke a suitable response in a human T cell, in particular for peptides of clinically significant antigens, there remains a need for in vivo and in vitro systems that mimic aspects of human immune system. Thus, there is a need for biological systems (e.g., genetically modified non-human animals and cells) that can display components of a human immune system.

SUMMARY OF THE INVENTION

A biological system for generating or identifying peptides that associate with human MHC class I proteins and chimeras thereof and bind CD8+ T cells, as well as peptides that associate with human MHC class II proteins and chimeras thereof and bind to CD4+ T cells, is provided. Non-human animals comprising non-human cells that express humanized molecules that function in the cellular immune response are provided. Humanized rodent loci that encode humanized MHC I and MHC II proteins are also provided. Humanized rodent cells that express humanized MHC molecules are also provided. In vivo and in vitro systems are provided that comprise humanized rodent cells, wherein the rodent cells express one or more humanized immune system molecules.

In various embodiments, provided herein is a non-human animal comprising at an endogenous MHC locus a first nucleotide sequence encoding a chimeric human/non-human MHC I polypeptide, wherein a human portion of the chimeric MHC I polypeptide comprises an extracellular domain of a human MHC I polypeptide; a second nucleotide sequence encoding a chimeric human/non-human MHC II α polypeptide, wherein a human portion of the chimeric human/non-human MHC II α polypeptide comprises an extracellular domain of a human MHC II a polypeptide; and a third nucleotide sequence encoding a chimeric human/non-human MHC II β polypeptide, wherein a human portion of the chimeric human/non-human MHC II β polypeptide comprises an extracellular domain of a human MHC II β polypeptide, wherein the non-human animal expresses functional chimeric human/non-human MHC I and MHC II proteins from its endogenous non-human MHC loci. In one embodiment, the animal does not express functional endogenous MHC I, II α, and/or II β polypeptides from the endogenous non-human MHC loci. In some embodiments, the animal is not capable of expressing functional endogenous MHC I, II α, and/or II β polypeptides, since for example, genes encoding endogenous MHC I and MHC II proteins may be functionally inactivated, e.g., are incapable of being transcribed and translated into endogenous MHC I and MHC II proteins, respectively. In various embodiments, all endogenous genes of the non-human animal encoding MHC molecules that are expressed on the cell surface (e.g., present antigen to and associate with T cell receptor) are functionally inactivated such that the animal does not express endogenous cell-surface MHC I, II α, and/or II β polypeptides. In some embodiments, genes may be functionally inactivated with a mutation (e.g., inversion), replacement of the gene (in whole or in part) and/or deletion of the gene (in whole or in part). In some embodiments, a non-human MHC class I gene may be functionally inactivated by the replacement of an endogenous sequence encoding α1, α2, and α3 domains of an endogenous MHC class I polypeptide with a sequence encoding α1, α2, and α3 domains of a human MHC class I polypeptide; a non-human MHC class II α gene may be inactivated by the replacement of an endogenous sequence encoding α1 and α2 domains of an endogenous MHC class II α polypeptide with a sequence encoding α1 and α2 domains of a human MHC class II α polypeptide; or a non-human MHC class II β gene may be inactivated by the replacement of an endogenous sequence encoding β1 and β2 domains of an endogenous MHC class II β polypeptide with a sequence encoding β1 and β2 domains of a human MHC class II β polypeptide.

In one aspect, the first nucleotide sequence is located at the endogenous non-human MHC I locus, the second nucleotide sequence is located at the endogenous non-human MHC II α locus, and the third nucleotide sequence is located at the endogenous non-human MHC II β locus. In one aspect, the first, second and/or third nucleotide sequence(s) are operably linked to endogenous non-human regulatory elements. In one aspect, the first nucleotide sequence is operably linked to endogenous non-human MHC I promoter and regulatory elements, the second nucleotide sequence is operably linked to endogenous non-human MHC II α promoter and regulatory elements, and the third nucleotide sequence is operably linked to endogenous non-human MHC β promoter and regulatory elements.

In one embodiment, the human portion of a chimeric MHC I polypeptide comprises α1, α2, and α3 domains of the human MHC I polypeptide. In one aspect, a non-human portion of the chimeric MHC I polypeptide comprises transmembrane and cytoplasmic domains of an endogenous non-human MHC I polypeptide. The human MHC I polypeptide may be selected from the group consisting of HLA-A, HLA-B, and HLA-C. In one embodiment, the human MHC I polypeptide is HLA-A2. In another aspect, the human MHC I polypeptide is HLA-A3, HLA-B7, HLA-B27, HLA-Cw6, or any other MHC I molecule expressed in a human population. In an additional embodiment, a non-human animal of the invention further comprises at its endogenous non-human β2 microglobulin locus a nucleotide sequence encoding a human or humanized β2 microglobulin polypeptide, wherein the animal expresses the human or humanized β2 microglobulin polypeptide.

In one embodiment, the human MHC II α extracellular domain comprises human MHC II α1 and α2 domains. In another embodiment, the human MHC II β extracellular domain comprises human MHC II β1 and β2 domains. In one aspect, the non-human portion of a chimeric human/non-human MHC II α polypeptide comprises transmembrane and cytoplasmic domains of an endogenous non-human MHC II α polypeptide. In one aspect, the non-human portion of a chimeric human/non-human MHC II β polypeptide comprises transmembrane and cytoplasmic domains of an endogenous non-human MHC II β polypeptide. In one embodiment, the human portions of a chimeric human/mouse MHC II α and β polypeptides are derived from a human HLA class II protein selected from the group consisting of HLA-DR, HLA-DQ, and HLA-DP. In one specific embodiment, the human portions of chimeric human/non-human MHC II α and β polypeptides are derived from a human HLA-DR2 protein. Alternatively, the human portions of chimeric human/non-human MHC II α and β polypeptides may be derived from human MHC II protein selected from HLA-DR4, HLA-DQ2.5, HLA-DQ8, or any other MHC II molecule expressed in a human population.

In some aspects, a provided animal comprises two copies of the MHC locus containing the first, the second, and the third nucleotide sequences, while in other aspects, a provided animal comprises one copy of the MHC locus containing the first, the second, and the third nucleotide sequences. Thus, the animal may be homozygous or heterozygous for the MHC locus containing nucleotide sequences encoding chimeric human/non-human MHC I, MHC II α, and MHC II β polypeptides. In some embodiments of the invention, the genetically modified MHC locus, comprising nucleotide sequences encoding chimeric human/non-human MHC I, MHC II α, and MHC II β polypeptides described herein, is in the germline of the non-human animal.

Also provided herein is an MHC locus comprising a first nucleotide sequence encoding a chimeric human/non-human MHC I polypeptide, wherein a human portion of the chimeric MHC I polypeptide comprises an extracellular domain of a human MHC I polypeptide; a second nucleotide sequence encoding a chimeric human/non-human MHC II α polypeptide, wherein a human portion of the chimeric human/non-human MHC II α polypeptide comprises an extracellular domain of a human MHC II α polypeptide; and a third nucleotide sequence encoding a chimeric human/non-human MHC II β polypeptide, wherein a human portion of the chimeric human/non-human MHC II β polypeptide comprises an extracellular domain of a human MHC II β polypeptide. In some aspects, non-human portions of the chimeric MHC I, II α, and II β polypeptides comprise transmembrane and cytoplasmic domains of non-human MHC I, II α, and II β, respectively.

In one embodiment, the genetically engineered non-human animal is a rodent. In one embodiment, the rodent is a rat or a mouse. In one embodiment, the rodent is a mouse. Thus, in one aspect, the first nucleotide sequence encodes a chimeric human/mouse MHC I polypeptide, and the mouse portion of the chimeric MHC I polypeptide is derived from H-2K, H-2D, or H-2L. In one specific embodiment, the mouse portion of the chimeric MHC I polypeptide is derived from H-2K. In one aspect, the second nucleotide sequence encodes a chimeric human/mouse MHC II α polypeptide, the third nucleotide sequence encodes a chimeric human/mouse MHC II β polypeptide, and the mouse portions of the chimeric MHC II α and β polypeptides are derived from H-2E or H-2A. In yet another embodiment, the mouse does not express any functional endogenous MHC II α and MHC II β polypeptides on a cell surface, and the only MHC II α and MHC II β polypeptides expressed on a cell surface are chimeric human/mouse MHC II α and MHC II β polypeptides. In a specific embodiment, the mouse portions of the chimeric MHC II polypeptides are derived from H-2E. In some embodiments, the mouse does not express functional endogenous MHC polypeptides from its H-2D locus. In some embodiments, the mouse is engineered to lack all or a portion of an endogenous H-2D locus. In some embodiments, the mouse does not express any endogenous MHC I and II polypeptides on a cell surface; in some embodiments, all endogenous mouse MHC I and II polypeptides that are expressed on a cell surface are functionally inactivated or fully or partially deleted.

Thus, also provided herein is a genetically engineered mouse comprising at an endogenous MHC locus a first nucleotide sequence encoding a chimeric human/mouse MHC I polypeptide, wherein the human portion of the chimeric MHC I polypeptide comprises an extracellular domain of a human MHC I polypeptide; a second nucleotide sequence encoding a chimeric human/mouse MHC II α polypeptide, wherein the human portion of the chimeric human/non-human MHC II α polypeptide comprises an extracellular domain of a human MHC II α polypeptide; and a third nucleotide sequence encoding a chimeric human/mouse MHC II β polypeptide, wherein the human portion of the chimeric human/non-human MHC II β polypeptide comprises an extracellular domain of a human MHC II β polypeptide; wherein the mouse expresses functional chimeric human/mouse MHC I and MHC II proteins from its endogenous mouse MHC locus. In one specific embodiment, the first nucleotide sequence encodes a chimeric HLA-A2/H-2K polypeptide, the second nucleotide sequence encodes an α chain of a chimeric HLA-DR/H-2E polypeptide (e.g., HLA-DR2/H-2E polypeptide), and the third nucleotide sequence encodes a β chain of a chimeric HLA-DR/H-2E polypeptide (e.g., HLA-DR2/H-2E polypeptide), and the mouse expresses functional HLA-A2/H-2K and HLA-DR/H-2E (e.g., HLA-DR2/H-2E) proteins. In an additional embodiment, the mouse further comprises at an endogenous β2 microglobulin locus a nucleotide sequence encoding a human or humanized β2 microglobulin polypeptide. In one embodiment, the mouse does not express functional endogenous MHC polypeptides from its endogenous MHC locus. In some embodiments, the mouse does not express functional MHC I or II polypeptides on a cell surface; in some embodiments, the only MHC I and MHC II polypeptides expressed on a cell surface are chimeric human/mouse MHC I and II polypeptides. In some embodiments, the mouse does not express functional endogenous MHC polypeptides from its H-2D locus. In some embodiments, the mouse is engineered to lack all or a portion of an endogenous H-2D locus. In yet another embodiment, the endogenous H-2D is deleted or functionally inactivated.

Also provided herein are methods for generating a genetically modified non-human animal (e.g., rodent, e.g., mouse or rat) described herein. Thus, in one aspect, the invention provides a method of generating a genetically modified non-human animal comprising replacing at an endogenous non-human MHC II locus a nucleotide sequence encoding a non-human MHC II complex with a nucleotide sequence encoding a chimeric human/non-human MHC II complex to generate a first non-human animal; and replacing at an endogenous non-human MHC I locus a nucleotide sequence encoding a non-human MHC I polypeptide with a nucleotide sequence encoding a chimeric human/non-human MHC I polypeptide to generate a second non-human animal. In one aspect, the steps of replacing nucleotide sequences comprise homologous recombination in non-human ES cells, and the second non-human animal is generated by homologous recombination in ES cells bearing nucleotide sequences encoding chimeric human/non-human MHC II complex. The chimeric MHC II complex comprises chimeric human/non-human MHC II α and β polypeptides. In some embodiments, ES cells are mouse ES cells engineered to lack all or a portion of an endogenous H-2D locus. In other embodiments, the ES cells are engineered to have a functionally inactivated H-2D locus. In yet another embodiments, the ES cells lack or are engineered to lack or have functional inactivation of all or a portion of endogenous H-2A, H-2E, H-2K, H-2D, and H-2L loci.

In an alternative embodiment, the invention provides a method of generating a genetically modified non-human animal comprising replacing at an endogenous non-human MHC I locus a nucleotide sequence encoding a non-human MHC I polypeptide with a nucleotide sequence encoding a chimeric human/non-human MHC I polypeptide to generate a first non-human animal; and replacing at an endogenous non-human MHC II locus a nucleotide sequence encoding a non-human MHC II complex with a nucleotide sequence encoding a chimeric human/non-human MHC II complex to generate a second non-human animal. In one aspect, the steps of replacing nucleotide sequences comprise homologous recombination in non-human ES cells, and the second non-human animal is generated by homologous recombination in ES cells bearing a nucleotide sequence encoding chimeric human/non-human MHC I polypeptide.

Also provided herein are cells, e.g., isolated antigen-presenting cells, derived from the non-human animals (e.g., rodents, e.g., mice or rats) described herein. Tissues and embryos derived from the non-human animals described herein are also provided.

Any of the embodiments and aspects described herein can be used in conjunction with one another, unless otherwise indicated or apparent from the context. Other embodiments will become apparent to those skilled in the art from a review of the ensuing detailed description. The following detailed description includes exemplary representations of various embodiments of the invention, which are not restrictive of the invention as claimed. The accompanying figures constitute a part of this specification and, together with the description, serve only to illustrate embodiments and not to limit the invention.

DETAILED DESCRIPTION OF EMBODIMENTS OF THE INVENTION

Definitions

Figure 1:
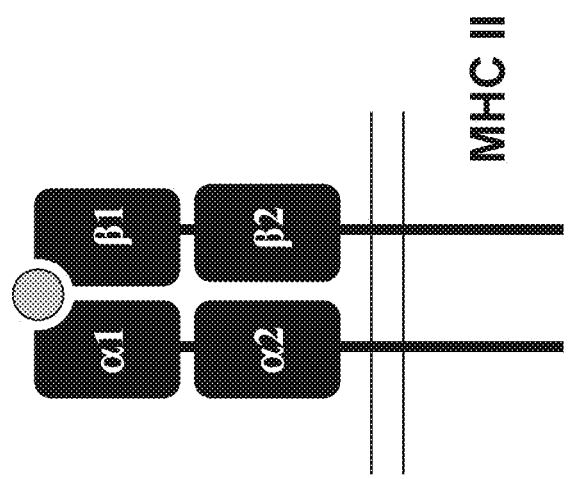
FIG. 1 is a schematic drawing of the MHC I (left panel) and MHC II (right panel) class molecules expressed on the surface of a cell. The gray circles represent peptides bound in the peptide-binding clefts.
Figure 1:
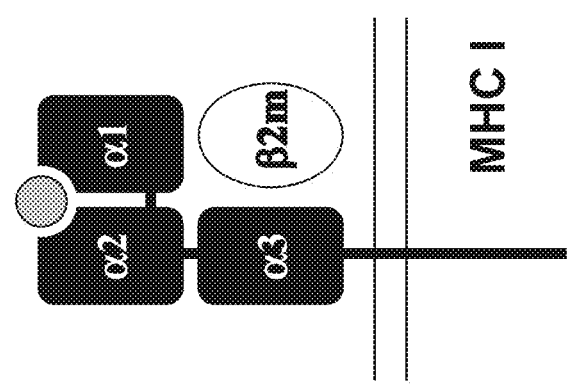

The present invention provides genetically modified non-human animals (e.g., mice, rats, rabbits, etc.) that express both human or humanized MHC I and MHC II proteins; embryos, cells, and tissues comprising the same; methods of making the same; as well as methods of using the same. Unless defined otherwise, all terms and phrases used herein include the meanings that the terms and phrases have attained in the art, unless the contrary is clearly indicated or clearly apparent from the context in which the term or phrase is used.

The term "conservative," when used to describe a conservative amino acid substitution, includes substitution of an amino acid residue by another amino acid residue having a side chain R group with similar chemical properties (e.g., charge or hydrophobicity). Conservative amino acid substitutions may be achieved by modifying a nucleotide sequence so as to introduce a nucleotide change that will encode the conservative substitution. In general, a conservative amino acid substitution will not substantially change the functional properties of interest of a protein, for example, the ability of MHC I or MHC II to present a peptide of interest. Examples of groups of amino acids that have side chains with similar chemical properties include aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. In some embodiments, a conservative amino acid substitution can be a substitution of any native residue in a protein with alanine, as used in, for example, alanine scanning mutagenesis. In some embodiments, a conservative substitution is made that has a positive value in the PAM250 log-likelihood matrix disclosed in Gonnet et al. ((1992) Exhaustive Matching of the Entire Protein Sequence Database, Science 256:1443-45), hereby incorporated by reference. In some embodiments, the substitution is a moderately conservative substitution wherein the substitution has a nonnegative value in the PAM250 log-likelihood matrix.

Thus, also encompassed by the invention is a genetically modified non-human animal whose genome comprises a nucleotide sequence encoding a human or humanized MHC I and II polypeptides, wherein MHC I or MHC II the polypeptide comprises conservative amino acid substitutions in the amino acid sequence described herein.

One skilled in the art would understand that in addition to the nucleic acid residues encoding a human or humanized MHC I or MHC II polypeptide described herein, due to the degeneracy of the genetic code, other nucleic acids may encode the polypeptide of the invention. Therefore, in addition to a genetically modified non-human animal that comprises in its genome a nucleotide sequence encoding MHC I and MHC II polypeptides with conservative amino acid substitutions, a non-human animal whose genome comprises a nucleotide sequence that differs from that described herein due to the degeneracy of the genetic code is also provided.

The term "identity" when used in connection with sequence includes identity as determined by a number of different algorithms known in the art that can be used to measure nucleotide and/or amino acid sequence identity. In some embodiments described herein, identities are determined using a ClustalW v. 1.83 (slow) alignment employing an open gap penalty of 10.0, an extend gap penalty of 0.1, and using a Gonnet similarity matrix (MacVector™ 10.0.2, MacVector Inc., 2008). The length of the sequences compared with respect to identity of sequences will depend upon the particular sequences. In various embodiments, identity is determined by comparing the sequence of a mature protein from its N-terminal to its C-terminal. In various embodiments when comparing a chimeric human/non-human sequence to a human sequence, the human portion of the chimeric human/non-human sequence (but not the non-human portion) is used in making a comparison for the purpose of ascertaining a level of identity between a human sequence and a human portion of a chimeric human/non-human sequence (e.g., comparing a human ectodomain of a chimeric human/mouse protein to a human ectodomain of a human protein).

The terms "homology" or "homologous" in reference to sequences, e.g., nucleotide or amino acid sequences, means two sequences which, upon optimal alignment and comparison, are identical in at least about 75% of nucleotides or amino acids, e.g., at least about 80% of nucleotides or amino acids, e.g., at least about 90-95% nucleotides or amino acids, e.g., greater than 97% nucleotides or amino acids. One skilled in the art would understand that, for optimal gene targeting, the targeting construct should contain arms homologous to endogenous DNA sequences (i.e., "homology arms"); thus, homologous recombination can occur between the targeting construct and the targeted endogenous sequence.

The term "operably linked" refers to a juxtaposition wherein the components so described are in a relationship permitting them to function in their intended manner. As such, a nucleic acid sequence encoding a protein may be operably linked to regulatory sequences (e.g., promoter, enhancer, silencer sequence, etc.) so as to retain proper transcriptional regulation. In addition, various portions of the chimeric or humanized protein of the invention may be operably linked to retain proper folding, processing, targeting, expression, and other functional properties of the protein in the cell. Unless stated otherwise, various domains of the chimeric or humanized protein of the invention are operably linked to each other.

The term "MHC I complex" or the like, as used herein, includes the complex between the MHC I α chain polypeptide and the β2-microglobulin polypeptide. The term "MHC I polypeptide" or the like, as used herein, includes the MHC I α chain polypeptide alone. The terms "MHC II complex," "MHC II protein," or the like, as used herein, include the complex between an MHC II α polypeptide and an MHC II β polypeptide. The term "MHC II α polypeptide" or "MHC II β polypeptide" (or the like), as used herein, includes the MHC II α polypeptide alone or MHC II β polypeptide alone, respectively. Similarly, the terms "HLA-DR4 complex", "HLA-DR4 protein," "H-2E complex," "H-2E protein," or the like, refer to complex between α and β polypeptides. Typically, the terms "human MHC" and "HLA" are used interchangeably.

The term "replacement" in reference to gene replacement refers to placing exogenous genetic material at an endogenous genetic locus, thereby replacing all or a portion of the endogenous gene with an orthologous or homologous nucleic acid sequence. As demonstrated in the Examples below, nucleic acid sequence of endogenous MHC locus was replaced by a nucleotide sequence comprising sequences encoding a portion of human MHC I polypeptide, specifically, encoding the extracellular portion of the MHC I polypeptide; as well as portions of human MHC II α and β polypeptides, specifically, encoding the extracellular portions of the MHC II α and β polypeptides.

"Functional" as used herein, e.g., in reference to a functional polypeptide, refers to a polypeptide that retains at least one biological activity normally associated with the native protein. For example, in some embodiments of the invention, a replacement at an endogenous locus (e.g., replacement at an endogenous non-human MHC locus) results in a locus that fails to express a functional endogenous polypeptide, e.g., MHC I or MHC II polypeptide. Likewise, the term "functional" as used herein in reference to functional extracellular domain of a protein, refers to an extracellular domain that retains its functionality, e.g., in the case of MHC I or MHC II, ability to bind an antigen, ability to bind a T cell co-receptor, etc. In reference to genes, an endogenous gene may be functionally inactivated by various techniques such that the whole gene or a portion of the gene that encodes an endogenous protein is still present at its locus but the gene is incapable of encoding an endogenous protein that is biologically active. In some embodiments of the invention, a replacement at the endogenous MHC locus results in a locus that fails to express an extracellular domain (e.g., a functional extracellular domain) of an endogenous MHC while expressing an extracellular domain (e.g., a functional extracellular domain) of a human MHC.

Genetically Modified MHC Animals

In various embodiments, the invention generally provides genetically modified non-human animals that comprise in their genome a nucleotide sequence encoding a human or humanized MHC I and MHC II polypeptides; thus, the animals express a human or humanized MHC I and MHC II polypeptides.

Figure 2:
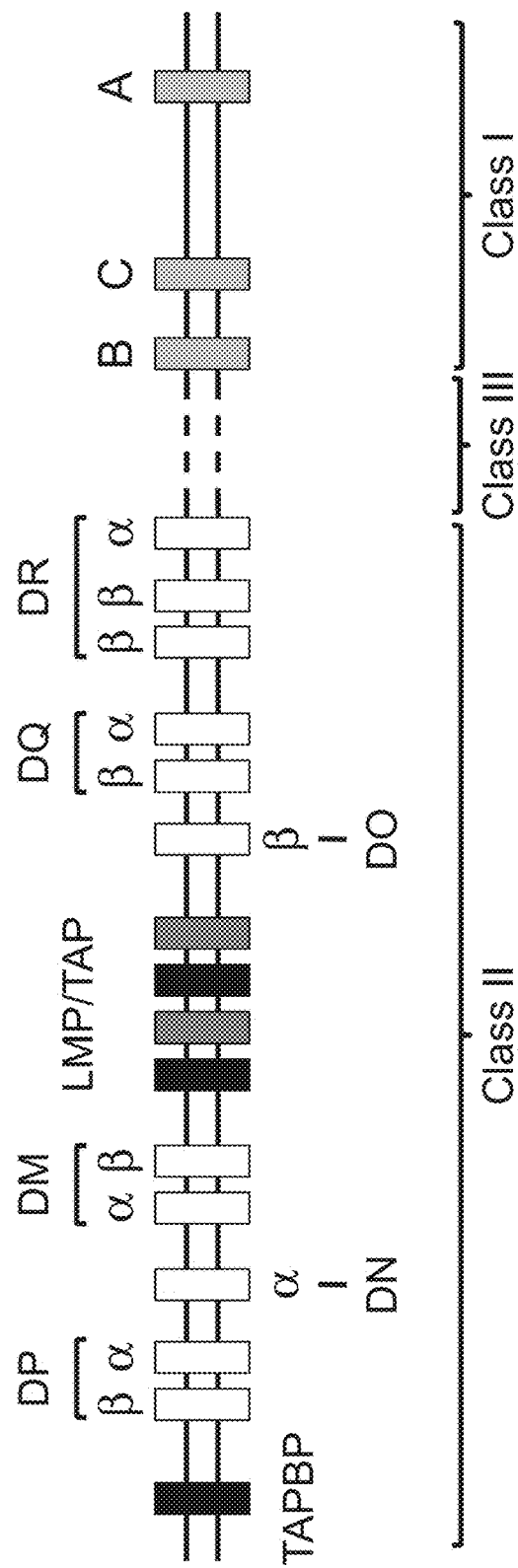
FIG. 2 is a schematic representation (not to scale) of the relative genomic structure of the human HLA, showing class I, II and III genes.
Figure 3:
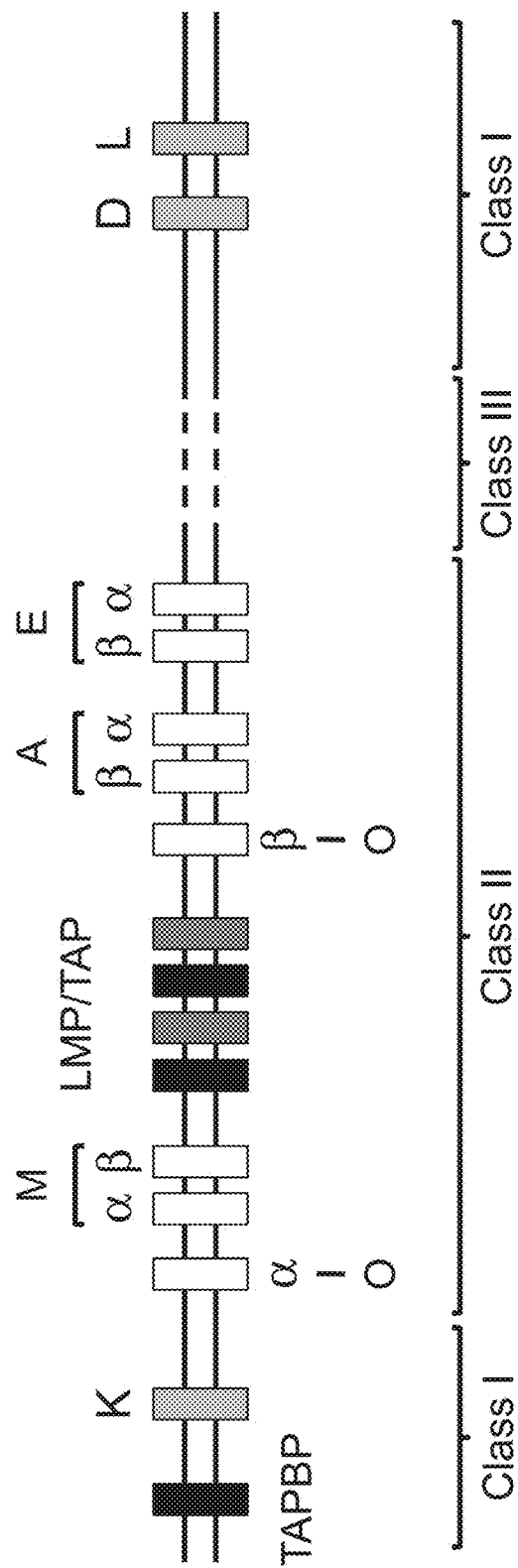
FIG. 3 is a schematic representation (not to scale) of the relative genomic structure of the mouse MHC, showing class I, II and III genes.

MHC genes are categorized into three classes: class I, class II, and class III, all of which are encoded either on human chromosome 6 or mouse chromosome 17. A schematic of the relative organization of the human and mouse MHC classes is presented in FIGS. 2 and 3, respectively. The MHC genes are among the most polymorphic genes of the mouse and human genomes. MHC polymorphisms are presumed to be important in providing evolutionary advantage; changes in sequence can result in differences in peptide binding that allow for better presentation of pathogens to cytotoxic T cells.

MHC class I protein comprises an extracellular domain (which comprises three domains: $\alpha_1$, $\alpha_2$, and $\alpha_3$), a transmembrane domain, and a cytoplasmic tail. The $\alpha_1$ and $\alpha_2$ domains form the peptide-binding cleft, while the $\alpha_3$ interacts with β2-microglobulin.

In addition to its interaction with β2-microglobulin, the $\alpha_3$ domain interacts with the TCR co-receptor CD8, facilitating antigen-specific activation. Although binding of MHC class I to CD8 is about 100-fold weaker than binding of TCR to MHC class I, CD8 binding enhances the affinity of TCR binding. Wooldridge et al. (2010) MHC Class I Molecules with Superenhanced CD8 Binding Properties Bypass the Requirement for Cognate TCR Recognition and Nonspecifically Activate CTLs, J. Immunol. 184:3357-3366. Interestingly, increasing MHC class I binding to CD8 abrogated antigen specificity in CTL activation. Id.

CD8 binding to MHC class I molecules is species-specific; the mouse homolog of CD8, Lyt-2, was shown to bind H-2D$^d$ molecules at the $\alpha_3$ domain, but it did not bind HLA-A molecules. Connolly et al. (1988) The Lyt-2 Molecule Recognizes Residues in the Class I $\alpha_3$ Domain in Allogeneic Cytotoxic T Cell Responses, J. Exp. Med. 168:325-341. Differential binding was presumably due to CDR-like determinants (CDR1- and CDR2-like) on CD8 that was not conserved between humans and mice. Sanders et al. (1991) Mutations in CD8 that Affect Interactions with HLA Class I and Monoclonal Anti-CD8 Antibodies, J. Exp. Med. 174:371-379; Vitiello et al. (1991) Analysis of the HLA-restricted Influenza-specific Cytotoxic T Lymphocyte Response in Transgenic Mice Carrying a Chimeric Human-Mouse Class I Major Histocompatibility Complex, J. Exp. Med. 173:1007-1015; and, Gao et al. (1997) Crystal structure of the complex between human CD8$\alpha\alpha$ and HLA-A2, Nature 387:630-634. It has been reported that CD8 binds HLA-A2 in a conserved region of the $\alpha_3$ domain (at position 223-229). A single substitution (V245A) in HLA-A reduced binding of CD8 to HLA-A, with a concomitant large reduction in T cell-mediated lysis. Salter et al. (1989), Polymorphism in the $\alpha_3$ domain of HLA-A molecules affects binding to CD8, Nature 338:345-348. In general, polymorphism in the $\alpha_3$ domain of HLA-A molecules also affected binding to CD8. Id. In mice, amino acid substitution at residue 227 in H-2D$^d$ affected the binding of mouse Lyt-2 to H-2D$^d$, and cells transfected with a mutant H-2D$^d$ were not lysed by CD8+ T cells. Potter et al. (1989) Substitution at residue 227 of H-2 class I molecules abrogates recognition by CD8-dependent, but not CD8-independent, cytotoxic T lymphocytes, Nature 337:73-75.

Therefore, due to species specificity of interaction between the MHC class I $\alpha_3$ domain and CD8, an MHC I complex comprising a replacement of an H-2K $\alpha_3$ domain with a human HLA-A2 $\alpha_3$ domain was nonfunctional in a mouse (i.e., in vivo) in the absence of a human CD8. In animals transgenic for HLA-A2, substitution of human $\alpha_3$ domain for the mouse $\alpha_3$ domain resulted in restoration of T cell response. Irwin et al. (1989) Species-restricted interactions between CD8 and the $\alpha_3$ domain of class I influence the magnitude of the xenogeneic response, J. Exp. Med. 170:1091-1101; Vitiello et al. (1991), supra.

The transmembrane domain and cytoplasmic tail of mouse MHC class I proteins also have important functions. One function of MHC I transmembrane domain is to facilitate modulation by HLA-A2 of homotypic cell adhesion (to enhance or inhibit adhesion), presumably as the result of cross-linking (or ligation) of surface MHC molecules. Wagner et al. (1994) Ligation of MHC Class I and Class II Molecules Can Lead to Heterologous Desensitization of Signal Transduction Pathways That Regulate Homotypic Adhesion in Human Lymphocytes, J. Immunol. 152:5275-5287. Cell adhesion can be affected by mAbs that bind at diverse epitopes of the HLA-A2 molecule, suggesting that there are multiple sites on HLA-A2 implicated in modulating homotypic cell adhesion; depending on the epitope bound, the affect can be to enhance or to inhibit HLA-A2-dependent adhesion. Id.

The cytoplasmic tail, encoded by exons 6 and 7 of the MHC I gene, is reportedly necessary for proper expression on the cell surface and for LIR1-mediated inhibition of NK cell cytotoxicity. Gruda et al. (2007) Intracellular Cysteine Residues in the Tail of MHC Class I Proteins Are Crucial for Extracellular Recognition by Leukocyte Ig-Like Receptor 1, J. Immunol. 179:3655-3661. A cytoplasmic tail is required for multimerizaton of at least some MHC I molecules through formation of disulfide bonds on its cysteine residues, and thus may play a role in clustering and in recognition by NK cells. Lynch et al. (2009) Novel MHC Class I Structures on Exosomes, J. Immunol. 183:1884-1891.

The cytoplasmic domain of HLA-A2 contains a constitutively phosphorylated serine residue and a phosphorylatable tyrosine, although—in Jurkat cells—mutant HLA-A2 molecules lacking a cytoplasmic domain appear normal with respect to expression, cytoskeletal association, aggregation, and endocytic internalization. Gur et al. (1997) Structural Analysis of Class I MHC Molecules: The Cytoplasmic Domain Is Not Required for Cytoskeletal Association, Aggregation, and Internalization, Mol. Immunol. 34(2):125-132. Truncated HLA-A2 molecules lacking the cytoplasmic domain are apparently normally expressed and associate with β2 microglobulin. Id.

However, several studies have demonstrated that the cytoplasmic tail is critical in intracellular trafficking, dendritic cell (DC)-mediated antigen presentation, and CTL priming. A tyrosine residue encoded by exon 6 was shown to be required for MHC I trafficking through endosomal compartments, presentation of exogenous antigens, and CTL priming; while deletion of exon 7 caused enhancement of anti-viral CTL responses. Lizee et al. (2003) Control of Dendritic Cross-Presentation by the Major Histocompatibility Complex Class I Cytoplasmic Domain, Nature Immunol. 4:1065-73; Basha et al. (2008) MHC Class I Endosomal and Lysosomal Trafficking Coincides with Exogenous Antigen Loading in Dendritic Cells, PLoS ONE 3: e3247; and Rodriguez-Cruz et al. (2011) Natural Splice Variant of MHC Class I Cytoplasmic Tail Enhances Dendritic Cell-Induced CD8+ T-Cell Responses and Boosts Anti-Tumor Immunity, PLoS ONE 6:e22939.

MHC class II complex comprises two non-covalently associated domains: an α chain and a β chain, also referred herein as an α polypeptide and a β polypeptide (FIG. 1, right). The protein spans the plasma membrane; thus it contains an extracellular domain, a transmembrane domain, and a cytoplasmic domain. The extracellular portion of the α chain includes α1 and α2 domains, and the extracellular portion of the β chain includes β1 and β2 domains. The α1 and β1 domains form a peptide-binding cleft on the cell surface. Due to the three-dimensional conformation of the peptide-binding cleft of the MHC II complex, there is theoretically no upper limit on the length of the bound antigen, but typically peptides presented by MHC II are between 13 and 17 amino acids in length.

In addition to its interaction with the antigenic peptides, the peptide-binding cleft of the MHC II molecule interacts with invariant chain (Ii) during the processes of MHC II complex formation and peptide acquisition. The α/β MHC II dimers assemble in the endoplasmic reticulum and associate with Ii chain, which is responsible for control of peptide binding and targeting of the MHC II into endocytic pathway. In the endosome, Ii undergoes proteolysis, and a small fragment of Ii, Class II-associated invariant chain peptide (CLIP), remains at the peptide-binding cleft. In the endosome, under control of HLA-DM (in humans), CLIP is exchanged for antigenic peptides.

MHC II interacts with T cell co-receptor CD4 at the hydrophobic crevice at the junction between α2 and β2 domains. Wang and Reinherz (2002) Structural Basis of T Cell Recognition of Peptides Bound to MHC Molecules, Molecular Immunology, 38:1039-49. When CD4 and T cell receptor bind the same MHC II molecule complexed with a peptide, the sensitivity of a T cell to antigen is increased, and it requires 100-fold less antigen for activation. See, Janeway's Immunobiology, $7^{th}$ Ed., Murphy et al. eds., Garland Science, 2008, incorporated herein by reference.

Numerous functions have been proposed for transmembrane and cytoplasmic domains of MHC II. In the case of cytoplasmic domain, it has been shown to be important for intracellular signaling, trafficking to the plasma membrane, and ultimately, antigen presentation. For example, it was shown that T cell hybridomas respond poorly to antigen-presenting cells (APCs) transfected with MHC II β chains truncated at the cytoplasmic domain, and induction of B cell differentiation is hampered. See, e.g., Smiley et al. (1996) Truncation of the class II β-chain cytoplasmic domain influences the level of class II/invariant chain-derived peptide complexes, Proc. Natl. Acad. Sci. USA, 93:241-44. Truncation of Class II molecules seems to impair cAMP production. It has been postulated that deletion of the cytoplasmic tail of MHC II affects intracellular trafficking, thus preventing the complex from coming across relevant antigens in the endocytic pathway. Smiley et al. (supra) demonstrated that truncation of class II molecules at the cytoplasmic domain reduces the number of CLIP/class II complexes, postulating that this affects the ability of CLIP to effectively regulate antigen presentation.

It has been hypothesized that, since MHC II clustering is important for T cell receptor (TCR) triggering, if MHC II molecules truncated at the cytoplasmic domain were prevented from binding cytoskeleton and thus aggregating, antigen presentation to T cells would be affected. Ostrand-Rosenberg et al. (1991) Abrogation of Tumorigenicity by MHC Class II Antigen Expression Requires the Cytoplasmic Domain of the Class II Molecule, J. Immunol. 147:2419-22. In fact, it was recently shown that HLA-DR truncated at the cytoplasmic domain failed to associate with the cytoskeleton following oligomerization. El Fakhy et al. (2004) Delineation of the HLA-DR Region and the Residues Involved in the Association with the Cytoskeleton, J. Biol. Chem. 279: 18472-80. Importantly, actin cytoskeleton is a site of localized signal transduction activity, which can effect antigen presentation. In addition to association with cytoskeleton, recent studies have also shown that up to 20% of all HLA-DR molecules constitutively reside in the lipid rafts of APCs, which are microdomains rich in cholesterol and glycosphingolipids, and that such localization is important for antigen presentation, immune synapse formation, and MHC II-mediated signaling. See, e.g., Dolan et al. (2004) Invariant Chain and the MHC II Cytoplasmic Domains Regulate Localization of MHC Class II Molecules to Lipid Rafts in Tumor Cell-Based Vaccines, J. Immunol. 172:907-14. Dolan et al. suggested that truncation of cytoplasmic domain of MHC II reduces constitutive localization of MHC II to lipid rafts.

In addition, the cytoplasmic domain of MHC II, in particular the β chain, contains a leucine residue that is subject to ubiquitination by ubiquitin ligase, membrane-associated RING-CH I (MARCH I), which controls endocytic trafficking, internalization, and degradation of MHC II; and it has been shown that MARCH-mediated ubiquitination ceases upon dendritic cell maturation resulting in increased levels of MHC II at the plasma membrane. Shin et al. (2006) Surface expression of MHC class II in dendritic cells is controlled by regulated ubiquitination, Nature 444: 115-18; De Gassart et al. (2008) MHC class II stabilization at the surface of human dendritic cells is the result of maturation-dependent MARCH I down-regulation, Proc. Natl. Acad. Sci. USA 105:3491-96.

Transmembrane domains of α and β chains of MHC II interact with each other and this interaction is important for proper assembly of class II MHC complex. Cosson and Bonifacino (1992) Role of Transmembrane Domain Interactions in the Assembly of Class II MHC Molecules, Nature 258:659-62. In fact, MHC II molecules in which the transmembrane domains of the α and β chains were replaced by the α chain of IL-2 receptor were retained in the ER and were barely detectable at the cell surface. Id. Through mutagenesis studies, conserved Gly residues at the α and β transmembrane domains were found to be responsible for MHC II assembly at the cell surface. Id. Thus, both transmembrane and cytoplasmic domains are crucial for the proper function of the MHC II complex.

In various embodiments, provided herein is a genetically modified non-human animal, e.g., rodent (e.g., mouse or rat) comprising in its genome a nucleotide sequence encoding a human or humanized MHC I polypeptide and a nucleotide sequence encoding human or humanized MHC II protein. The MHC I nucleotide sequence may encode an MHC I polypeptide that is partially human and partially non-human, e.g., chimeric human/non-human MHC I polypeptide, and the MHC II nucleotide sequence may encode an MHC II protein that is partially human and partially non-human, e.g., chimeric human/non-human MHC II protein (e.g., comprising chimeric human/non-human MHC II α and β polypeptides). In some aspects, the animal does not express endogenous MHC I and II polypeptides, e.g., functional endogenous MHC I and II polypeptides. In some embodiments, the only MHC I and MHC II molecules expressed on a cell surface of the animal are chimeric MHC I and II molecules.

A genetically modified non-human animal comprising in its genome, e.g., at the endogenous locus, a nucleotide sequence encoding a chimeric human/non-human MHC I polypeptide is disclosed in U.S. Patent Application Publication Nos. 20130111617 and 20130185819, which applications are incorporated herein by reference in their entireties. A genetically modified non-human animal comprising in its genome, e.g., at the endogenous locus, a nucleotide sequence encoding humanized, e.g., chimeric human/non-human MHC II polypeptides is disclosed in U.S. Pat. Nos.

8,847,005 and 9,043,996, which applications are incorporated herein by reference in their entireties. A genetically modified non-human animal comprising in its genome, e.g., at the endogenous locus, a nucleotide sequence encoding a chimeric human/non-human MHC I polypeptide and comprising in its genome, e.g., at the endogenous locus, a nucleotide sequence encoding humanized, e.g., chimeric human/non-human MHC II polypeptides, is disclosed in U.S. Patent Application Publication No. 20140245467, which application is incorporated herein by reference in its entirety.

In various embodiments provided herein is a genetically modified non-human animal comprising in its genome, e.g., at endogenous MHC locus, a first nucleotide sequence encoding a chimeric human/non-human MHC I polypeptide, wherein a human portion of the chimeric MHC I polypeptide comprises an extracellular domain of a human MHC I polypeptide; a second nucleotide sequence encoding a chimeric human/non-human MHC II α polypeptide, wherein a human portion of the chimeric MHC II α polypeptide comprises an extracellular domain of a human MHC II α polypeptide; and a third nucleotide sequence encoding a chimeric human/non-human MHC II β polypeptide, wherein a human portion of the chimeric MHC II β polypeptide comprises an extracellular domain of a human MHC II β polypeptide; wherein the non-human animal expresses functional chimeric human/non-human MHC I and MHC II proteins from its endogenous non-human MHC locus. In one embodiment, the first, second, and/or third nucleotide sequences are located the endogenous non-human MHC locus. In one embodiment, wherein the non-human animal is a mouse, the first, second, and/or third nucleotide sequences are located at the endogenous mouse MHC locus on mouse chromosome 17. In one embodiment, the first nucleotide sequence is located at the endogenous non-human MHC I locus. In one embodiment, the second nucleotide sequence is located at the endogenous non-human MHC II α locus. In one embodiment, the third nucleotide sequence is located at the endogenous non-human MHC II β locus.

In one embodiment, the non-human animal only expresses the chimeric human/non-human MHC I, MHC II α and/or MHC β II polypeptides and does not express endogenous non-human MHC polypeptides (e.g., functional endogenous MHC I, II α and/or II β polypeptides) from the endogenous non-human MHC locus. In one embodiment, the animal described herein expresses a functional chimeric MHC I and a functional chimeric MHC II on the surface of its cells, e.g., antigen presenting cells, etc. In one embodiment, the only MHC I and MHC II expressed by the animal on a cell surface are chimeric MHC I and chimeric MHC II, and the animal does not express any endogenous MHC I and MHC II on a cell surface.

In one embodiment, the chimeric human/non-human MHC I polypeptide comprises in its human portion a peptide binding domain of a human MHC I polypeptide. In one aspect, the human portion of the chimeric polypeptide comprises an extracellular domain of a human MHC I. In this embodiment, the human portion of the chimeric polypeptide comprises an extracellular domain of an α chain of a human MHC I. In one embodiment, the human portion of the chimeric polypeptide comprises α1 and α2 domains of a human MHC I. In another embodiment, the human portion of the chimeric polypeptide comprises α1, α2, and α3 domains of a human MHC I.

In one aspect, a human portion of the chimeric MHC II α polypeptide and/or a human portion of the chimeric MHC II β polypeptide comprises a peptide-binding domain of a human MHC II α polypeptide and/or human MHC II β polypeptide, respectively. In one aspect, a human portion of the chimeric MHC II α and/or β polypeptide comprises an extracellular domain of a human MHC II α and/or β polypeptide, respectively. In one embodiment, a human portion of the chimeric MHC II α polypeptide comprises α1 domain of a human MHC II α polypeptide; in another embodiment, a human portion of the chimeric MHC II α polypeptide comprises α1 and α2 domains of a human MHC II α polypeptide. In an additional embodiment, a human portion of the chimeric MHC II β polypeptide comprises β1 domain of a human MHC II β polypeptide; in another embodiment, a human portion of the chimeric MHC II β polypeptide comprises β1 and β2 domains of a human MHC II β polypeptide.

In some embodiments, the human or humanized MHC I polypeptide may be derived from a functional human HLA molecule encoded by any of HLA-A, HLA-B, HLA-C, HLA-E, HLA-F, or HLA-G loci. The human or humanized MHC II polypeptide may be derived from a functional human HLA molecule encoded by an of HLA-DP, -DQ, and -DR loci. A list of commonly used HLA antigens and alleles is described in Shankarkumar et al. ((2004) The Human Leukocyte Antigen (HLA) System, Int. J. Hum. Genet. 4(2):91-103), incorporated herein by reference. Shankarkumar et al. also present a brief explanation of HLA nomenclature used in the art. Additional information regarding HLA nomenclature and various HLA alleles can be found in Holdsworth et al. (2009) The HLA dictionary 2008: a summary of HLA-A, -B, -C, -DRB1/3/4/5, and DQB1 alleles and their association with serologically defined HLA-A, -B, -C, -DR, and -DQ antigens, Tissue Antigens 73:95-170, and a recent update by Marsh et al. (2010) Nomenclature for factors of the HLA system, 2010, Tissue Antigens 75:291-455, both incorporated herein by reference. In some embodiments, the MHC I or MHC II polypeptides may be derived from any functional human HLA-A, B, C, DR, or DQ molecules. Thus, the human or humanized MHC I and/or II polypeptides may be derived from any functional human HLA molecules described therein. In some embodiments, all MHC I and MHC II polypeptides expressed on a cell surface comprise a portion derived from human HLA molecules.

Of particular interest are human HLA molecules, specific polymorphic HLA alleles, known to be associated with a number of human diseases, e.g., human autoimmune diseases. In fact, specific polymorphisms in HLA loci have been identified that correlate with development of rheumatoid arthritis, type I diabetes, Hashimoto's thyroiditis, multiple sclerosis, myasthenia gravis, Graves' disease, systemic lupus erythematosus, celiac disease, Crohn's disease, ulcerative colitis, and other autoimmune disorders. See, e.g., Wong and Wen (2004) What can the HLA transgenic mouse tell us about autoimmune diabetes?, Diabetologia 47:1476-87; Taneja and David (1998) HLA Transgenic Mice as Humanized Mouse Models of Disease and Immunity, J. Clin. Invest. 101:921-26; de Bakker et al. (2006), A high-resolution HLA and SNP haplotype map for disease association studies in the extended human MHC, Nature Genetics 38:1166-72 and Supplementary Information; and International MHC and Autoimmunity Genetics Network (2009) Mapping of multiple susceptibility variants within the MHC region for 7 immune-mediated diseases, Proc. Natl. Acad. Sci. USA 106:18680-85. Thus, the human or humanized MHC I and/or II polypeptides may be derived from a human HLA molecule known to be associated with a particular disease, e.g., autoimmune disease.

In one specific aspect, the human or humanized MHC I polypeptide is derived from human HLA-A. In a specific embodiment, the HLA-A polypeptide is an HLA-A2 polypeptide (e.g., and HLA-A2.1 polypeptide). In one embodiment, the HLA-A polypeptide is a polypeptide encoded by an HLA-A*0201 allele, e.g., HLA-A*02:01:01:01 allele. The HLA-A*0201 allele is commonly used amongst the North American population. Although the present Examples describe this particular HLA sequence, any suitable HLA-A sequence is encompassed herein, e.g., polymorphic variants of HLA-A2 exhibited in human population, sequences with one or more conservative or non-conservative amino acid modifications, nucleic acid sequences differing from the sequence described herein due to the degeneracy of genetic code, etc.

In another specific aspect, the human portion of the chimeric MHC I polypeptide is derived from human MHC I selected from HLA-B and HLA-C. In one aspect, it is derived from HLA-B, e.g., HLA-B27. In another aspect, it is derived from HLA-A3, -B7, -Cw6, etc.

In one specific aspect, the human portions of the humanized MHC II α and β polypeptides described herein are derived from human HLA-DR, e.g., HLA-DR2. Typically, HLA-DR α chains are monomorphic, e.g., the α chain of HLA-DR complex is encoded by HLA-DRA gene (e.g., HLA-DRα*01 gene). On the other hand, the HLA-DR β chain is polymorphic. Thus, HLA-DR2 comprises an α chain encoded by HLA-DRA gene and a β chain encoded by HLA-DR1β*1501 gene. Although the present Examples describe these particular HLA sequences, any suitable HLA-DR sequences are encompassed herein, e.g., polymorphic variants exhibited in human population, sequences with one or more conservative or non-conservative amino acid modifications, nucleic acid sequences differing from the sequences described herein due to the degeneracy of genetic code, etc.

The human portions of the chimeric MHC II α and/or β polypeptide may be encoded by nucleotide sequences of HLA alleles known to be associated with common human diseases. Such HLA alleles include, but are not limited to, HLA-DRB1*0401, -DRB1*0301, -DQA1*0501, -DQB1*0201, -DRB1*1501, -DRB1*1502, -DQB1*0602, -DQA1*0102, -DQA1*0201, -DQB1*0202, -DQA1*0501, and combinations thereof. For a summary of HLA allele/disease associations, see de Bakker et al. (2006), supra, incorporated herein by reference.

In one aspect, the non-human portion of a chimeric human/non-human MHC I, MHC II α and/or MHC II β polypeptide(s) comprises transmembrane and/or cytoplasmic domains of an endogenous non-human (e.g., rodent, e.g., mouse, rat, etc.) MHC I, MHC II α and/or MHC II β polypeptide(s), respectively. Thus, the non-human portion of the chimeric human/non-human MHC I polypeptide may comprise transmembrane and/or cytoplasmic domains of an endogenous non-human MHC I polypeptide. The non-human portion of a chimeric MHC II α polypeptide may comprise transmembrane and/or cytoplasmic domains of an endogenous non-human MHC II α polypeptide. The non-human portion of a chimeric human/non-human MHC II β polypeptide may comprise transmembrane and/or cytoplasmic domains of an endogenous non-human MHC II β polypeptide. In one aspect, the non-human animal is mouse, and a non-human portion of the chimeric MHC I polypeptide is derived from a mouse H-2K protein. In one aspect, the animal is a mouse, and non-human portions of the chimeric MHC II α and β polypeptides are derived from a mouse H-2E protein. Thus, a non-human portion of the chimeric MHC I polypeptide may comprise transmembrane and cytoplasmic domains derived from a mouse H-2K, and non-human portions of the chimeric MHC II α and β polypeptides may comprise transmembrane and cytoplasmic domains derived from a mouse H-2E protein. Although specific H-2K and H-2E sequences are contemplated in the Examples, any suitable sequences, e.g., polymorphic variants, conservative/non-conservative amino acid substitutions, etc., are encompassed herein. In one aspect, the non-human animal is a mouse, and the mouse does not express functional endogenous MHC polypeptides from its H-2D locus. In some embodiments, the mouse is engineered to lack all or a portion of an endogenous H-2D locus. In other aspects, the mouse does not express any functional endogenous mouse MHC I and MHC II on a cell surface.

A chimeric human/non-human polypeptide may be such that it comprises a human or a non-human leader (signal) sequence. In one embodiment, the chimeric MHC I polypeptide comprises a non-human leader sequence of an endogenous MHC I polypeptide. In one embodiment, the chimeric MHC II α polypeptide comprises a non-human leader sequence of an endogenous MHC II α polypeptide. In one embodiment, the chimeric MHC II β polypeptide comprises a non-human leader sequence of an endogenous MHC II β polypeptide. In an alternative embodiment, the chimeric MHC I, MHC II α and/or MHC II β polypeptide(s) comprises a non-human leader sequence of MHC I, MHC II α and/or MHC II β polypeptide(s), respectively, from another non-human animal, e.g., another rodent or another mouse strain. Thus, the nucleotide sequence encoding the chimeric MHC I, MHC II α and/or MHC II β polypeptide may be operably linked to a nucleotide sequence encoding a non-human MHC I, MHC II α and/or MHC II β leader sequence, respectively. In yet another embodiment, the chimeric MHC I, MHC II α and/or MHC II β polypeptide(s) comprises a human leader sequence of human MHC I, human MHC II α and/or human MHC II β polypeptide, respectively (e.g., a leader sequence of human HLA-A2, human HLA-DRA and/or human HLA-DRβ1*1501, respectively).

A chimeric human/non-human MHC I, MHC II α and/or MHC II β polypeptide may comprise in its human portion a complete or substantially complete extracellular domain of a human MHC I, human MHC II α and/or human MHC II β polypeptide, respectively. Thus, a human portion may comprise at least 80%, preferably at least 85%, more preferably at least 90%, e.g., 95% or more of the amino acids encoding an extracellular domain of a human MHC I, human MHC II α and/or human MHC II β polypeptide (e.g., human HLA-A2, human HLA-DRA and/or human HLA-DRβ1*1501). In one example, substantially complete extracellular domain of the human MHC I, human MHC II α and/or human MHC II β polypeptide lacks a human leader sequence. In another example, the chimeric human/non-human MHC I, chimeric human/non-human MHC II α and/or the chimeric human/non-human MHC II β polypeptide comprises a human leader sequence.

Moreover, the chimeric MHC I, MHC II α and/or MHC II β polypeptide may be operably linked to (e.g., be expressed under the regulatory control of) endogenous non-human promoter and regulatory elements, e.g., mouse MHC I, MHC II α and/or MHC II β regulatory elements, respectively. Such arrangement will facilitate proper expression of the chimeric MHC I and/or MHC II polypeptides in the non-human animal, e.g., during immune response in the non-human animal.

The genetically modified non-human animal may be selected from a group consisting of a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo.

In one aspect, the non-human animal is a mammal. In one aspect, the non-human animal is a small mammal, e.g., of the superfamily Dipodoidea or Muroidea. In one embodiment, the genetically modified animal is a rodent. In one embodiment, the rodent is selected from a mouse, a rat, and a hamster. In one embodiment, the rodent is selected from the superfamily Muroidea. In one embodiment, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, white-tailed rats, Malagasy rats and mice), Platacanthomyidae (e.g., spiny dormice), and Spalacidae (e.g., mole rats, bamboo rats, and zokors). In a specific embodiment, the genetically modified rodent is selected from a true mouse or rat (family Muridae), a gerbil, a spiny mouse, and a crested rat. In one embodiment, the genetically modified mouse is from a member of the family Muridae. In one embodiment, the animal is a rodent. In a specific embodiment, the rodent is selected from a mouse and a rat. In one embodiment, the non-human animal is a mouse.

In one embodiment, the non-human animal is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In another embodiment, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2 (see, e.g., Festing et al. (1999) Revised nomenclature for strain 129 mice, Mammalian Genome 10:836, see also, Auerbach et al (2000) Establishment and Chimera Analysis of 129/SvEv- and C57BL/6-Derived Mouse Embryonic Stem Cell Lines). In one embodiment, the genetically modified mouse is a mix of an aforementioned 129 strain and an aforementioned C57BL/6 strain. In another embodiment, the mouse is a mix of aforementioned 129 strains, or a mix of aforementioned BL/6 strains. In one embodiment, the 129 strain of the mix is a 129S6 (129/SvEvTac) strain. In another embodiment, the mouse is a BALB strain, e.g., BALB/c strain. In yet another embodiment, the mouse is a mix of a BALB strain and another aforementioned strain. In some embodiments, the mouse strain is such that a genetically wild-type mouse of that strain only expresses MHC I polypeptides derived from H-2K and H-2D on a cell surface and lacks endogenous H-2L gene.

In one embodiment, the non-human animal is a rat. In one embodiment, the rat is selected from a Wistar rat, an LEA strain, a Sprague Dawley strain, a Fischer strain, F344, F6, and Dark Agouti. In one embodiment, the rat strain is a mix of two or more strains selected from the group consisting of Wistar, LEA, Sprague Dawley, Fischer, F344, F6, and Dark Agouti.

Thus, in one embodiment, the invention relates to a genetically modified mouse that comprises in its genome a first nucleotide sequence encoding a chimeric human/mouse MHC I, a second nucleotide sequence encoding a chimeric human/mouse MHC II α, and a third nucleotide sequence encoding a chimeric human/mouse MHC II β polypeptides. A human portion of the chimeric MHC I, MHC II α, and MHC II β may comprise an extracellular domain of a human MHC I, MHC II α, and MHC II β, respectively. In one embodiment, the mouse expresses functional chimeric human/mouse MHC I, MHC II α, and MHC II β polypeptides from its endogenous mouse MHC locus. In one embodiment, the mouse does not express functional mouse MHC polypeptides, e.g., functional mouse MHC I, MHC II α, and MHC II β polypeptides, from its endogenous mouse MHC locus. In one embodiment, the mouse does not express functional endogenous MHC polypeptides from its H-2D locus. In some embodiments, the mouse is engineered to lack all or a portion of an endogenous H-2D locus. In other embodiments, the only MHC I and MHC II expressed by the mouse on a cell surface are chimeric MHC I and II.

In one embodiment, a human portion of the chimeric human/mouse MHC I polypeptide comprises a peptide binding domain or an extracellular domain of a human MHC I (e.g., human HLA-A, e.g., human HLA-A2, e.g., human HLA-A2.1). In some embodiments, the mouse does not express a peptide binding or an extracellular domain of an endogenous mouse MHC I polypeptide from its endogenous mouse MHC I locus. The peptide binding domain of the chimeric human/mouse MHC I may comprise human α1 and α2 domains. Alternatively, the peptide binding domain of the chimeric human/mouse MHC I may comprise human α1, α2, and α3 domains. In one aspect, the extracellular domain of the chimeric human/mouse MHC I comprises an extracellular domain of a human MHC I α chain. In one embodiment, the endogenous mouse MHC I locus is an H-2K (e.g., H-2Kb) locus, and the mouse portion of the chimeric MHC I polypeptide comprises transmembrane and cytoplasmic domains of a mouse H-2K (e.g., H-2Kb) polypeptide. Thus, in one embodiment, the mouse of the invention comprises at its endogenous mouse MHC I locus a nucleotide sequence encoding a chimeric human/mouse MHC I, wherein a human portion of the chimeric polypeptide comprises an extracellular domain of a human HLA-A2 (e.g., HLA-A2.1) polypeptide and a mouse portion comprises transmembrane and cytoplasmic domains of a mouse H-2K (e.g., H-2Kb) polypeptide, and a mouse expresses a chimeric human/mouse HLA-A2/H-2K protein. In other embodiment, the mouse portion of the chimeric MHC I polypeptide may be derived from other mouse MHC I, e.g., H-2D, H-2L, etc.; and the human portion of the chimeric MHC I polypeptide may be derived from other human MHC I, e.g., HLA-B, HLA-C, etc. In one aspect, the mouse does not express a functional endogenous H-2K polypeptide from its endogenous mouse H-2K locus. In one embodiment, the mouse does not express functional endogenous MHC polypeptides from its H-2D locus. In some embodiments, the mouse is engineered to lack all or a portion of an endogenous H-2D locus. In other embodiments, the only MHC I polypeptides expressed by the mouse on a cell surface are chimeric human/mouse MHC I polypeptides.

In one embodiment, a human portion of the chimeric human/mouse MHC II α polypeptide comprises a human MHC II α peptide binding or extracellular domain and a human portion of the chimeric human/mouse MHC II β polypeptide comprises a human MHC II β peptide binding or extracellular domain. In some embodiments, the mouse does not express a peptide binding or an extracellular domain of endogenous mouse α and/or β polypeptide from an endogenous mouse locus (e.g., H-2A and/or H-2E locus). In some embodiments, the mouse comprises a genome that lacks a gene that encodes a functional MHC class II molecule comprising an H-2Ab1, H-2Aa, H-2Eb1, H-2Eb2, H-2Ea, and a combination thereof. In some embodiments, the only MHC II polypeptides expressed by the mouse on a cell surface are chimeric human/mouse MHC II polypeptides. The peptide-binding domain of the chimeric human/mouse MHC II α polypeptide may comprise human α1 domain and the peptide-binding domain of the chimeric human/mouse MHC II β polypeptide may comprise a human β1 domain; thus, the peptide-binding domain of the chimeric MHC II complex may comprise human α1 and β1 domains. The extracellular domain of the chimeric human/mouse MHC II α polypeptide may comprise human α1 and α2 domains and the extracellular domain of the chimeric human/mouse MHC II β polypeptide may comprise human β1 and β2 domains; thus, the extracellular domain of the chimeric MHC II complex may comprise human α1, α2, β1 and β2 domains. In one embodiment, the mouse portion of the chimeric MHC II complex comprises transmembrane and cytosolic domains of mouse MHC II, e.g. mouse H-2E (e.g., transmembrane and cytosolic domains of mouse H-2E α and β chains). Thus, in one embodiment, the mouse of the invention comprises at its endogenous mouse MHC II locus a nucleotide sequence encoding a chimeric human/mouse MHC II α, wherein a human portion of the chimeric MHC II α polypeptide comprises an extracellular domain derived from an α chain of a human MHC II (e.g., α chain of HLA-DR2) and a mouse portion comprises transmembrane and cytoplasmic domains derived from an α chain of a mouse MHC II (e.g., H-2E); and a mouse comprises at its endogenous mouse MHC II locus a nucleotide sequence encoding a chimeric human/mouse MHC II β, wherein a human portion of the chimeric MHC II β polypeptide comprises an extracellular domain derived from a β chain of a human MHC II (e.g., β chain of HLA-DR2) and a mouse portion comprises transmembrane and cytoplasmic domains derived from a β chain of a mouse MHC II (e.g., H-2E); wherein the mouse expresses a chimeric human/mouse HLA-DR2/H-2E protein. In other embodiment, the mouse portion of the chimeric MHC II protein may be derived from other mouse MHC II, e.g., H-2A, etc.; and the human portion of the chimeric MHC II protein may be derived from other human MHC II, e.g., HLA-DQ, etc. In one aspect, the mouse does not express functional endogenous H-2A and H-2E polypeptides from their endogenous mouse loci (e.g., the mouse does not express H-2Ab1, H-2Aa, H-2Eb1, H-2Eb2, and H-2Ea polypeptides). In one aspect, the mouse does not express functional endogenous MHC polypeptides from its H-2D locus. In some embodiments, the mouse is engineered to lack all or a portion of an endogenous H-2D locus. In some embodiments, the mouse lacks expression of any endogenous MHC I or MHC II molecule on a cell surface.

In a further embodiment, a non-human animal of the invention, e.g., a rodent, e.g., a mouse, comprises at an endogenous β2 microglobulin locus a nucleotide sequence encoding a human or humanized β2 microglobulin. β2 microglobulin or the light chain of the MHC class I complex (also abbreviated "(β2M") is a small (12 kDa) non-glycosylated protein, that functions primarily to stabilize the MHC I α chain. Generation of human or humanized microglobulin animals is described in detail in U.S. Patent Publication No. 20130111617, and is incorporated herein by reference. A mouse comprising a humanized MHC locus as described in the present disclosure, and a human or humanized β2 microglobulin locus as described in U.S. Patent Publication No. 20130111617, may be generated by any methods known in the art, e.g., breeding, or alternatively, using homologous recombination in ES cells.

Various other embodiments of a genetically modified non-human animal, e.g. rodent, e.g., rat or mouse, would be evident to one skilled in the art from the present disclosure and from the disclosure of U.S. Patent Publication No. 20130111617 and U.S. Pat. No. 8,847,005 incorporated herein by reference.

In various aspects of the invention, the sequence(s) encoding a chimeric human/non-human MHC I and MHC II polypeptides are located at an endogenous non-human MHC locus (e.g., mouse H-2K and/or H-2E locus). In one embodiment, this results in a replacement of an endogenous MHC gene(s) or a portion thereof with a nucleotide sequence(s) encoding a human or humanized MHC I or MHC II polypeptides. Since the nucleotide sequences encoding MHC I, MHC II α and MHC II β polypeptides are located in proximity to one another on the chromosome, in order to achieve the greatest success in humanization of both MHC I and MHC II in one animal, the MHC I and MHC II loci should be targeted sequentially. Thus, also provided herein are methods of generating a genetically modified non-human animal comprising nucleotide sequences encoding chimeric human/non-human MHC I, MHC II α and MHC II β polypeptides as described herein.

In some embodiments, the method utilizes a targeting construct made using VELOCIGENE® technology, introducing the construct into ES cells, and introducing targeted ES cell clones into a mouse embryo using VELOCIMOUSE® technology, as described in the Examples.

The nucleotide constructs used for generating non-human animals described herein are also provided. In one aspect, the nucleotide construct comprises: 5' and 3' non-human homology arms, a human DNA fragment comprising human MHC gene sequences (e.g., human HLA-A2 or human HLA-DR4 gene sequences), and a selection cassette flanked by recombination sites. In one embodiment, the human DNA fragment is a genomic fragment that comprises both introns and exons of a human MHC gene (e.g., human HLA-A2 or HLA-DR2 gene). In one embodiment, the non-human homology arms are homologous to a non-human MHC locus (e.g., MHC I or MHC II locus).

A selection cassette is a nucleotide sequence inserted into a targeting construct to facilitate selection of cells (e.g., ES cells) that have integrated the construct of interest. A number of suitable selection cassettes are known in the art. Commonly, a selection cassette enables positive selection in the presence of a particular antibiotic (e.g., Neo, Hyg, Pur, CM, Spec, etc.). In addition, a selection cassette may be flanked by recombination sites, which allow deletion of the selection cassette upon treatment with recombinase enzymes. Commonly used recombination sites are loxP and Frt, recognized by Cre and Flp enzymes, respectively, but others are known in the art. In one embodiment, the selection cassette is located at the 5' end the human DNA fragment. In another embodiment, the selection cassette is located at the 3' end of the human DNA fragment. In another embodiment, the selection cassette is located within the human DNA fragment. In another embodiment, the selection cassette is located within an intron of the human DNA fragment.

In one embodiment, the 5' and 3' non-human homology arms comprise genomic sequence at 5' and 3' locations, respectively, of an endogenous non-human (e.g., murine) MHC class I or class II gene locus (e.g., 5' of the first leader sequence and 3' of the α3 exon of the mouse MHC I gene, or upstream of mouse H-2Ab1 gene and downstream of mouse H-2Ea gene). In one embodiment, the endogenous MHC class I locus is selected from mouse H-2K, H-2D and H-2L. In a specific embodiment, the endogenous MHC class I locus is mouse H-2K. In one embodiment, the endogenous MHC II locus is selected from mouse H-2E and H-2A. In one embodiment, the engineered MHC II construct allows replacement of both mouse H-2E and H-2A genes. In one embodiment, the mouse does not express functional endogenous MHC polypeptides from its H-2D locus. In some embodiments, the mouse is engineered to lack all or a portion of an endogenous H-2D locus. In another embodiment, the mouse does not express any functional endogenous MHC I and MHC II polypeptides on a cell surface. In one embodiment, the only MHC I and MHC II expressed by the mouse on a cell surface are chimeric human/mouse MHC I and MHC II.

Thus, in one embodiment, provided herein is a method of generating a genetically engineered non-human animal (e.g., rodent, e.g., rat or mouse) capable of expressing humanized MHC I and II proteins comprising replacing at an endogenous non-human MHC II locus a nucleotide sequence encoding a non-human MHC II complex with a nucleotide sequence encoding a chimeric human/non-human MHC II complex to generate a first non-human animal; and replacing at an endogenous non-human MHC I locus a nucleotide sequence encoding a non-human MHC I polypeptide with a nucleotide sequence encoding a chimeric human/non-human MHC I polypeptide to generate a second non-human animal. In one embodiment, the steps of replacing nucleotide sequences comprise homologous recombination in ES cells. In one embodiment, the second non-human animal is generated by homologous recombination in ES cells bearing nucleotide sequences encoding chimeric human/non-human MHC II complex. In one embodiment, the non-human animal is a mouse, and the first or second mouse does not express functional endogenous MHC polypeptides from its H-2D locus. In some embodiments, the first or second mouse is engineered to lack all or a portion of an endogenous H-2D locus. Alternatively, also provided herein is a method of generating a genetically engineered non-human animal (e.g., rodent, e.g., rat or mouse) capable of expressing humanized MHC I and II proteins comprising replacing at an endogenous non-human MHC I locus a nucleotide sequence encoding a non-human MHC I polypeptide with a nucleotide sequence encoding a chimeric human/non-human MHC I polypeptide to generate a first non-human animal; and replacing at an endogenous non-human MHC II locus a nucleotide sequence encoding a non-human MHC II complex with a nucleotide sequence encoding a chimeric human/non-human MHC II complex to generate a second non-human animal. In such embodiment, the second non-human animal is generated by homologous recombination in ES cells bearing a nucleotide sequence encoding chimeric human/non-human MHC I polypeptide.

Upon completion of gene targeting, ES cells or genetically modified non-human animals are screened to confirm successful incorporation of exogenous nucleotide sequence of interest or expression of exogenous polypeptide. Numerous techniques are known to those skilled in the art, and include (but are not limited to) Southern blotting, long PCR, quantitative PCT (e.g., real-time PCR using TAQMAN®), fluorescence in situ hybridization, Northern blotting, flow cytometry, Western analysis, immunocytochemistry, immunohistochemistry, etc. In one example, non-human animals (e.g., mice) bearing the genetic modification of interest can be identified by screening for loss of mouse allele and/or gain of human allele using a modification of allele assay described in Valenzuela et al. (2003) High-throughput engineering of the mouse genome coupled with high-resolution expression analysis, Nature Biotech. 21(6):652-659. Other assays that identify a specific nucleotide or amino acid sequence in the genetically modified animals are known to those skilled in the art.

In one aspect, a cell that expresses a chimeric human/non-human MHC I and MHC II proteins (e.g., HLA-A2/H-2K and HLA-DR2/H-2E proteins) is provided. In one aspect, the cell is a mouse cell that does not express functional endogenous MHC polypeptides from its H-2D locus. In some embodiments, the cell is a mouse cell is engineered to lack all or a portion of an endogenous H-2D locus. In some embodiments, the cell is a mouse cell that does not express any endogenous MHC I and MHC II polypeptide on its surface. In one embodiment, the cell comprises an expression vector comprising a chimeric MHC class I sequence and chimeric MHC class II sequence as described herein. In one embodiment, the cell is selected from CHO, COS, 293, HeLa, and a retinal cell expressing a viral nucleic acid sequence (e.g., a PERC.6™ cell).

A chimeric MHC II complex comprising an extracellular domain of HLA-DR2 described herein may be detected by anti-HLA-DR antibodies. Thus, a cell displaying chimeric human/non-human MHC II polypeptide may be detected and/or selected using anti-HLA-DR antibody. The chimeric MHC I complex comprising an extracellular domain of HLA-A2 described herein may be detected using anti-HLA-A, e.g., anti-HLA-A2 antibodies. Thus, a cell displaying a chimeric human/non-human MHC I polypeptide may be detected and/or selected using anti-HLA-A antibody. Antibodies that recognize other HLA alleles are commercially available or can be generated, and may be used for detection/selection.

Although the Examples that follow describe a genetically engineered animal whose genome comprises a replacement of a nucleotide sequence encoding mouse H-2K, and H-2A and H-2E proteins with a nucleotide sequence encoding a chimeric human/mouse HLA-A2/H-2K and HLA-DR2/H-2E protein, respectively, one skilled in the art would understand that a similar strategy may be used to introduce chimeras comprising other human MHC I and II genes (other HLA-A, HLA-B, and HLA-C; and other HLA-DR, HLA-DP and HLA-DQ genes). Such animals comprising multiple chimeric human/non-human (e.g., human/rodent, e.g., human/mouse) MHC I and MHC II genes at endogenous MHC loci are also provided.

In various embodiments of the invention, the mouse that comprises chimeric human/mouse MHC I and MHC II loci and expresses only chimeric human/mouse MHC I and MHC II on a cell surface (and lacks cell surface expression of any endogenous MHC I and MHC II) displays essentially normal B to T cell ratio, e.g., B to T cell ratio in the spleen. In some embodiments of the invention, the mouse described herein displays normal T and B cell development, expression levels, and expression patterns. In some embodiments of the invention, the mouse described herein expresses chimeric human/mouse MHC II only on antigen presenting cells of the mouse. In some embodiments, a mouse described herein elicits an immune response, e.g., a cellular immune response, to one or more human antigens. In some embodiments, a mouse described herein elicits a T cell response to one or more human antigens.

In various embodiments, the genetically modified non-human animals described herein make cells, e.g., APCs, with human or humanized MHC I and II on the cell surface and, as a result, present peptides as epitopes for T cells in a human-like manner, because substantially all of the components of the complex are human or humanized. The genetically modified non-human animals of the invention can be used to study the function of a human immune system in the humanized animal; for identification of antigens and antigen epitopes that elicit immune response (e.g., T cell epitopes, e.g., unique human cancer epitopes), e.g., for use in vaccine development; for evaluation of vaccine candidates and other vaccine strategies; for studying human autoimmunity; for studying human infectious diseases; and otherwise for devising better therapeutic strategies based on human MHC expression.

EXAMPLES

The invention will be further illustrated by the following nonlimiting examples. These Examples are set forth to aid in the understanding of the invention but are not intended to, and should not be construed to, limit its scope in any way. The Examples do not include detailed descriptions of conventional methods that would be well known to those of ordinary skill in the art (molecular cloning techniques, etc.). Unless indicated otherwise, parts are parts by weight, molecular weight is average molecular weight, temperature is indicated in Celsius, and pressure is at or near atmospheric.

Example 1: Engineering a Mouse Comprising Humanized MHC I and MHC II Loci

Figure 4:
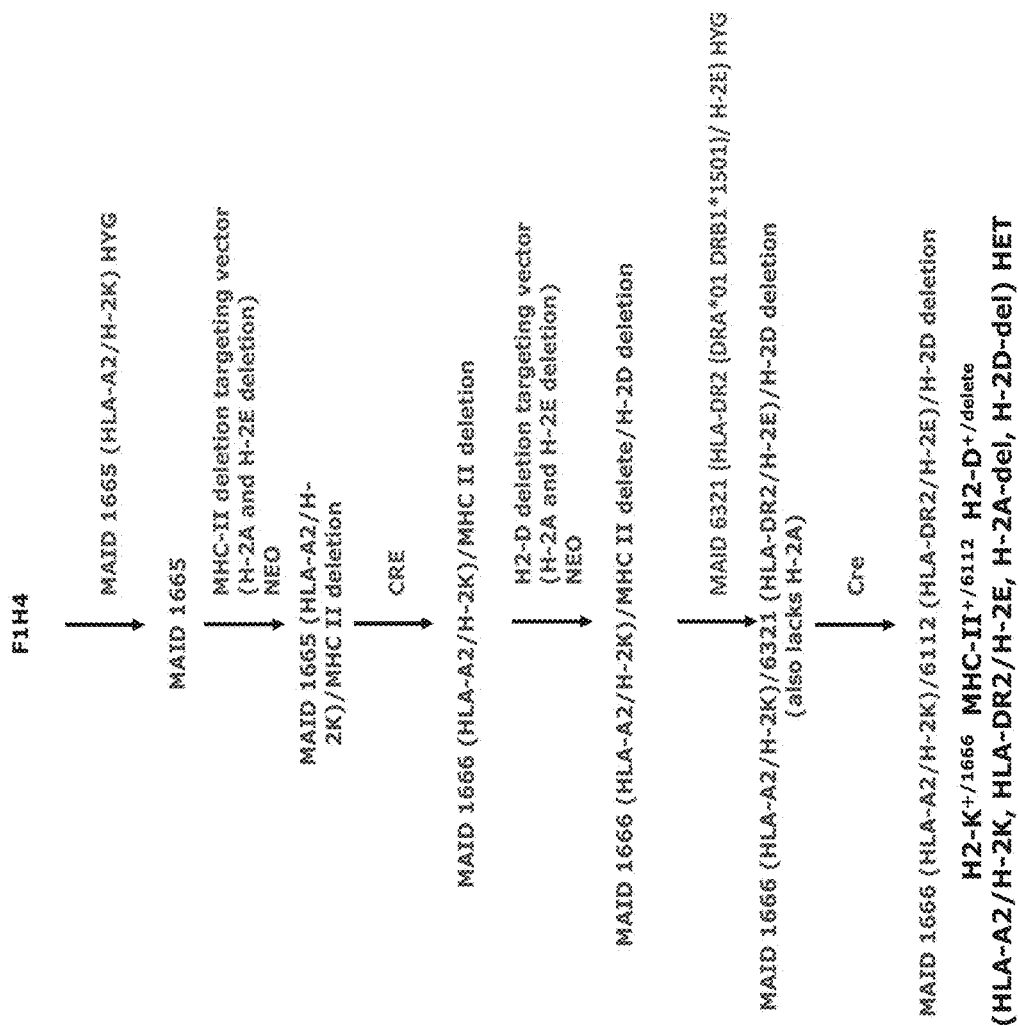
FIG. 4 depicts the strategy for generating a humanized MHC locus comprising humanized MHC I and MHC II genes. In the particular embodiment depicted, the MHC locus of the generated mouse comprises chimeric HLA-A2/H-2K and HLA-DR2/H-2E sequences (H2-K$^{+/1666}$ MHC-II$^{+/6112}$) and lacks H2-D sequence (H2-D$^{+/delete}$) and H-2A sequence (the genetic engineering scheme also results in a deletion of H-2A, see Example 1.2). Large Targeting Vectors introduced into ES cells at each stage of humanization are depicted to the right of the arrows.

The various steps involved in engineering a mouse comprising humanized MHC I and MHC II loci, with corresponding and additional endogenous MHC I and MHC II loci deletions (HLA-A2/H-2K, HLA-DR2/H-2E, H-2A-del, H-2D-del) are depicted in FIG. 4. Detailed description of the steps appears below.

Example 1.1: Engineering Mouse ES Cells Comprising Humanized MHC I Gene

Figure 5:
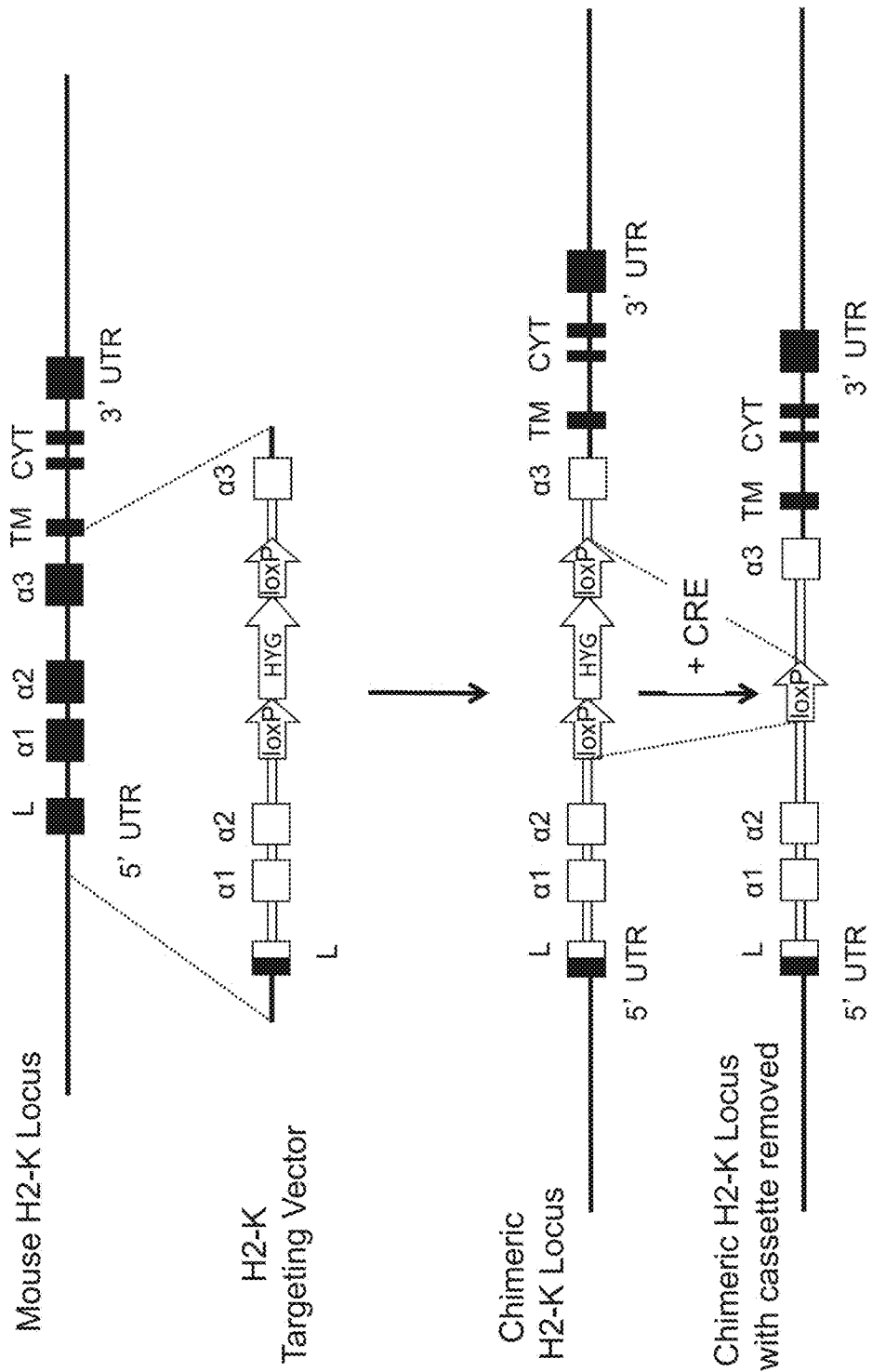
FIG. 5 is a schematic diagram (not to scale) of the targeting strategy used for making a chimeric H-2K locus that expresses an extracellular region of a human HLA-A2 protein. Mouse sequences are represented in black and human sequences are represented in white. L=leader, UTR=untranslated region, TM=transmembrane domain, CYT=cytoplasmic domain, HYG=hygromycin.

The mouse H-2K gene was humanized in a single step by construction of a unique targeting vector from human and mouse bacterial artificial chromosome (BAC) DNA using VELOCIGENE® technology (see, e.g., U.S. Pat. No. 6,586,251 and Valenzuela et al. (2003) High-throughput engineering of the mouse genome coupled with high-resolution expression analysis. Nat. Biotech. 21(6): 652-659). DNA from mouse BAC clone RP23-173k21 (Invitrogen) was modified by homologous recombination to replace the genomic DNA encoding the α1, α2 and α3 domains of the mouse H-2K gene with human genomic DNA encoding the α1, α2 and α3 subunits of the human HLA-A2 gene (FIG. 5). Detailed steps for construction of BAC DNA can be found in U.S. Patent Application Publication No. 2013-0111617, incorporated herein by reference. The targeted BAC DNA was used to electroporate mouse F1H4 ES cells to create modified ES cells for generating mice that express a chimeric MHC class I protein on the surface of nucleated cells (e.g., T and B lymphocytes, macrophages, neutrophils). ES cells containing an insertion of human HLA sequences were identified by a the quantitative PCR assay using TAQMAN™ (Lie and Petropoulos (1998) Curr. Opin. Biotechnology 9:43-48). Detailed steps for construction of mouse ES cells comprising humanized MHC I gene as well as screening can be also found in the same U.S. Patent Application Publication No. 2013-0111617.

ES cells comprising the chimeric HLA-A2/H-2K were utilized in further genetic engineering steps detailed below and in FIG. 4.

Example 1.2: Engineering Mouse ES Cells Comprising Deletion of MHC II Loci

The targeting vector for introducing a deletion of the endogenous MHC class II H-2Ab1, H-2Aa, H-2Eb1, H-2Eb2, and H-2Ea genes was made using VELOCIGENE® genetic engineering technology (see, e.g., U.S. Pat. No. 6,586,251 and Valenzuela et al., supra). Bacterial Artificial Chromosome (BAC) RP23-458i22 (Invitrogen) DNA was modified to delete the endogenous MHC class II genes H-2Ab1, H-2Aa, H-2Eb1, H-2Eb2, and H-2Ea.

Briefly, upstream and downstream homology arms were derived by PCR of mouse BAC DNA from locations 5' of the H-2Ab1 gene and 3' of the H-2Ea gene, respectively. These homology arms were used to make a cassette that deleted ~79 kb of RP23-458i22 comprising genes H-2Ab1, H-2Aa, H-2Eb1, H-2Eb2, and H-2Ea of the MHC class II locus by bacterial homologous recombination (BHR). This region was replaced with a neomycin cassette flanked by lox2372 sites. The final targeting vector included from 5' to 3' a 26 kb homology arm comprising mouse genomic sequence 5' to the H-2Ab1 gene of the endogenous MHC class II locus, a 5' lox2372 site, a neomycin cassette, a 3' lox2372 site and a 63 kb homology arm comprising mouse genomic sequence 3' to the H-2Ea gene of the endogenous MHC class II locus (MAID 5092).

The BAC DNA targeting vector (described above) was used to electroporate mouse ES cells comprising humanized MHC I locus (from Example 1.1 above) to create modified ES cells comprising a deletion of the endogenous MHC class II locus (both H-2A and H-2E were deleted). Positive ES cells containing a deleted endogenous MHC class II locus were identified by the quantitative PCR assay using TAQMAN™ probes (Lie and Petropoulos (1998) Curr. Opin. Biotechnology 9:43-48). The upstream region of the deleted locus was confirmed by PCR using primers 5111U F (CAGAACGCCAGGCTGTAAC; SEQ ID NO:1) and 5111U R (GGAGAGCAGGGTCAGTCAAC; SEQ ID NO:2) and probe 5111U P (CACCGCCACTCACAGCTC-CTTACA; SEQ ID NO:3), whereas the downstream region of the deleted locus was confirmed using primers 5111D F (GTGGGCACCATCTTCATCATTC; SEQ ID NO:4) and 5111D R (CTTCCTTTCCAGGGTGTGACTC; SEQ ID NO:5) and probe 5111D P (AGGCCTGCGATCAGGTG-GCACCT; SEQ ID NO:6). The presence of the neomycin cassette from the targeting vector was confirmed using primers NEOF (GGTGGAGAGGCTATTCGGC; SEQ ID NO:7) and NEOR (GAACACGGCGGCATCAG; SEQ ID NO:8) and probe NEOP (TGGGCACAACAGACAATCG-GCTG; SEQ ID NO:9). The nucleotide sequence across the upstream deletion point (SEQ ID NO:10) included the following, which indicates endogenous mouse sequence upstream of the deletion point (contained within the parentheses below) linked contiguously to cassette sequence present at the deletion point: (TTTGTAAACA AAGTC-TACCC AGAGACAGAT GACAGACTTC AGCTC-CAATG CTGATTGGTT CCTCACTTGG GACCAAC-CCT) ACCGGTATAA CTTCGTATAA GGTATCCTAT ACGAAGTTAT ATGCATGGCC TCCGCGCCGG. The nucleotide sequence across the downstream deletion point (SEQ ID NO:11) included the following, which indicates cassette sequence contiguous with endogenous mouse sequence downstream of the deletion point (contained within the parentheses below): CGACCTGCAG CCG-GCGCGCC ATAACTTCGT ATAAGGTATC CTATAC-GAAG TTATCTCGAG (CACAGGCATT TGGGTGGGCA GGGATGGACG GTGACTGGGA CAATCGGGAT GGAAGAGCAT AGAATGGGAG TTAGGGAAGA).

Subsequently to generation of the ES cells comprising both the MHC I humanization and endogenous MHC II deletion described above, the loxed neomycin cassette was removed using CRE. Specifically, a plasmid encoding Cre recombinase was electroporated into ES cells to remove the neomycin cassette.

Example 1.3: Generation of Mouse ES Cells Comprising H2-D Locus Deletion

To delete mouse H-2D locus, BHR was used to modify mouse BAC clone bMQ-218H21 (Sanger Institute), replacing 3756 bp of the H2-D gene (from the ATG start codon to 3 bp downstream of the TGA stop codon, exons 1-8 of mouse H-2D) with a 6,085 bp cassette containing from 5' to 3': a LacZ gene in frame with a 5' loxp site, UbC promoter, Neomycin gene, and 3' loxp site.

The BAC DNA targeting vector (described above) was used to electroporate mouse ES cells comprising humanized MHC I locus and a deletion of mouse MHC II, described in Example 1.2 above. Positive ES cells containing a deleted endogenous H-2D locus were identified by the quantitative PCR assay, as described above. Table 1 contains primers and probes used for the quantitative PCR assay.

TABLE 1

TAQMAN™ Loss of Allele Assay Primers and Probes

| Name (location) | Forward Primer | Reverse Primer | Probe |
|---|---|---|---|
| 5152 mTU (upstream) | CGAGGAGCCCCG GTACA (SEQ ID NO: 12) | AAGCGCACGAACTC CTTGTT (SEQ ID NO: 13) | CTCTGTCGGCTAT GTGG (SEQ ID NO: 14) |
| 5152 mTD (downstream) | GGACTCCCAGAAT CTCCTGAGA (SEQ ID NO: 15) | GAGTCATGAACCAT CACTGTGAAGA (SEQ ID NO: 16) | TGGTGGGTTGCTG GAA (SEQ ID NO: 17) |

Example 1.4: Generation of Mouse ES Cells Comprising Humanized MHC II Locus

To generate a vector comprising humanized HLA-DR2/H-2E, first, mouse H-2Ea gene was modified in accordance with the description in US Patent Application Publication No. US 2013-0111616, incorporated herein by reference, to generate a vector comprising sequence encoding a chimeric H-2Ea/HLA-DRA1*01 protein.

For mouse H-2Eb gene, synthesized human HLA-DR2 β chain (DRB1*1501) was used to generate a vector comprising DRβ1*02(1501) exons and introns, and swapped using bacterial homologous recombination into the vector comprising chimeric H-2Ea/HLA-DRA1*01 protein. H-2Eb gene was modified essentially as described in U.S. Patent Application Publication Nos. US 2013-0111616 and US 2013-0185820, incorporated herein by reference. A hygromycin selection cassette was used.

Figure 6:
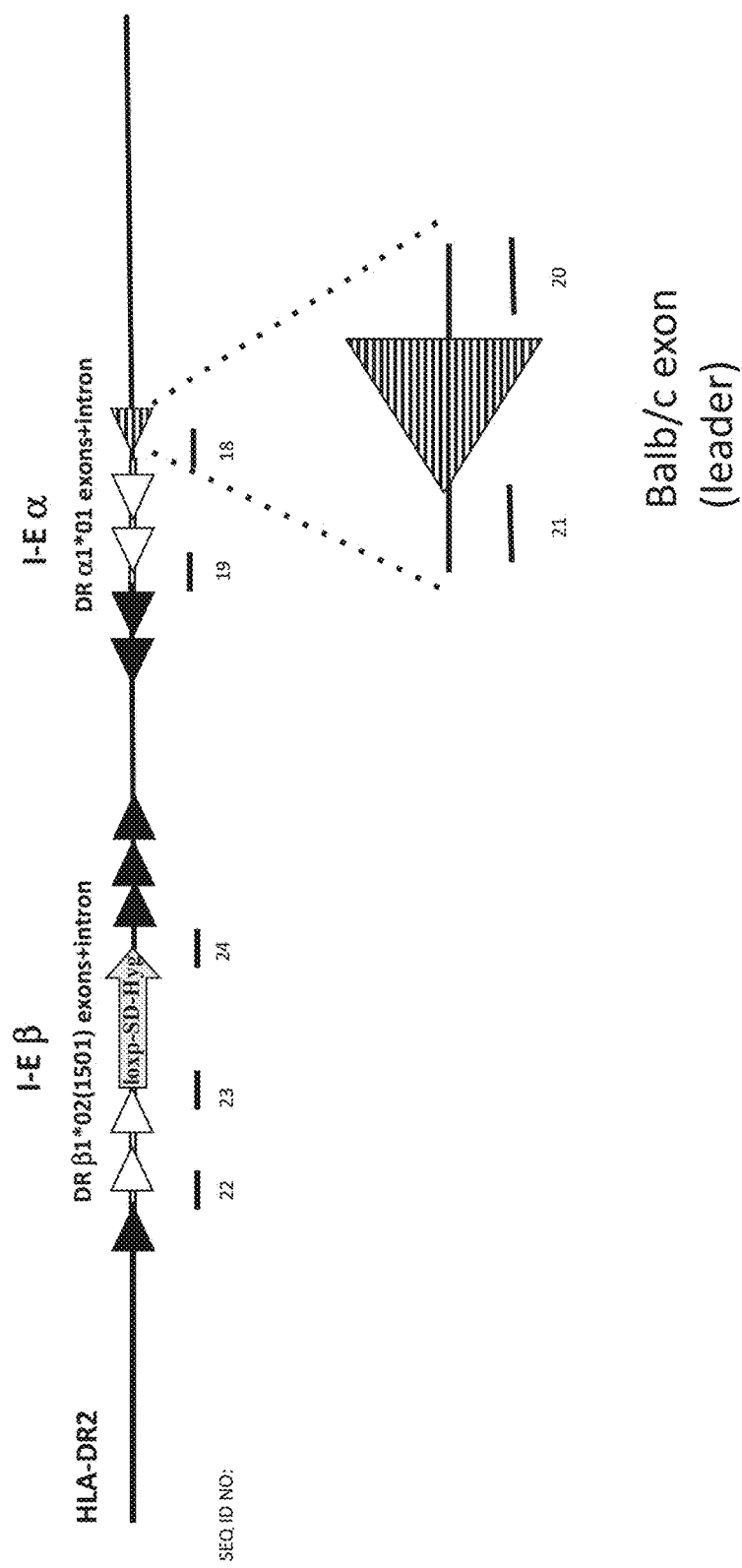
FIG. 6 is a schematic diagram of an exemplary HLA-DR2/H-2E large targeting vector.

The resulting HLA-DR2/H-2E LTVEC is depicted in FIG. 6. The various nucleotide sequence junctions of the resulting LTVECs (e.g., mouse/human sequence junctions, human/mouse sequence junctions, or junctions of mouse or human sequence with selection cassettes) are summarized below in Table 2 and listed in the Sequence Listing; their locations are indicated in the schematic diagram of FIG. 6. In Table 2 below, with the exception of sequences marked with asterisks (*, see Table legend) the mouse sequences are in regular font; the human sequences are in parentheses; the Lox sequences are italicized; and the restriction sites introduced during cloning steps and other vector-based sequences (e.g., multiple cloning sites, etc.) are bolded.

TABLE 2

Nucleotide Sequence Junctions

| SEQ ID NO: | Nucleotide Sequence |
|---|---|
| 18 | CTGTTTCTTC CCTAACTCCC ATTCTATGCT CTTCCATCCC GA CCGCGG(CCCA ATCTCTCTCC ACTACTTCCT GCCTACATGT ATGTAGGT) |
| 19 | (CAAGGTTTCC TCCTATGATG CTTGTGTGAA ACTCGG) GGCC GGCC AGCATTTAAC AGTACAGGGA TGGGAGCACA GCTCAC |
| 20* | (GAAAGCAGTC TTCCCAGCCT TCACACTCAG AGGTACAAAT) CCCCATTTTC ATATTAGCGA TTTTAATTTA TTCTAGCCTC |
| 21* | TCTTCCCTAA CTCCCATTCT ATGCTCTTCC ATCCCGA CCG CGG (CCCAATC TCTCTCCACT ACTTCCTGCC TACATGTATG) |
| 22 | GAGTTCCTCCATCACTTCACTGGGTAGCACAGCTGTAACTGT CCAGCCTG(TCCTGGGCTGCAGGTGGTGGGCGTTGCGGGTGG GGCCGGTTAAGGTTCCA) |
| 23 | (TCCCACATCCTATTTTAATTTGCTCCATGTTCTCATCTCCA TCAGCACAG)CTCGAG *ATAACTTCGTATAATGTATGCTATA CGAAGTTAT* ATGCATGGCC |
| 24 | *ATACGAAGTTAT* GCTAGTAACTATAACGGTCCTAAGGTAGC GAGTGGCTT ACAGGTAGGTGCGTGAAGCTTCTACAAGCACA GTTGCCCCCTGGGAAGCA |

*Sequences marked with asterisk are C57BL/6-BALB/c junction sequences where C57BL/6 sequences are in parentheses. During cloning of the chimeric H-2Ea gene, exon 1 and the remainder of intron 1 of the C57BL/6 allele of H-2Ea was replaced with the equivalent 2616 bp region from the BALB/c allele of H-2Ea. This was done because exon 1 of the C57BL/6 allele of H-2Ea contains a deletion which renders the gene nonfunctional, while exon 1 of BALB/c allele of H-2Ea is functional. For a more detailed description, see U.S. patent application Publication No. US 2013-0111616, incorporated herein by reference.

The targeted BAC DNA described above was used to electroporate mouse ES cells comprising humanized MHC I (HLA-A2), as well as MHC II and H-2D deletion to create modified ES cells for generating mice that express chimeric MHC I and MHC II genes and lack functional endogenous mouse H-2E, H-2A, H-2K, and H-2D loci. ES cells containing an insertion of human HLA sequences were identified by a quantitative PCR (TAQMAN™) assay, using primers and probes in Table 3 and the procedure described above.

TABLE 3

TAQMAN™ Primer and Probe Sequences

| Name (location) | Forward Primer | Reverse Primer | Probe |
|---|---|---|---|
| Hyg cassette | TGCGGCCGATC TTAGCC (SEQ ID NO: 25) | TTGACCGATTCC TTGCGG (SEQ ID NO: 26) | ACGAGCGGGTT CGGCCCATTC (SEQ ID NO: 27) |
| 7092 hTUP1 (Exon 2 of DRB1*1501) | CCCCACAGCAC GTTTCCT (SEQ ID NO: 28) | CGTCCCATTGAA GAAATGACACT (SEQ ID NO: 29) | TGGCAGCCTAA GAGG (SEQ ID NO: 30) |
| 7092 hTUP2 (Exon 2 of DRB1*1501) | CCCCACAGCAC GTTTCCT (SEQ ID NO: 31) | ACCCGCTCCGTC CCATT (SEQ ID NO: 32) | AGCCTAAGAGG GAGTGTC (SEQ ID NO: 33) |
| 7092 hTDP1 (Exon 3 of DRB1*1501) | AGACCCTGGTG ATGCTGGAA (SEQ ID NO: 34) | CGCTTGGGTGCT CCACTT (SEQ ID NO: 35) | TCGAAGTGGAG AGGTTTA (SEQ ID NO: 36) |
| 7092 hTDP2 (exon 3 of DRB1*1501) | TGGAATGGAGT GAGCAGCTTT (SEQ ID NO: 37) | GCACGGTCCCCT TCTTAGTG (SEQ ID NO: 38) | TGACTTCCTAAA TTTCTC (SEQ ID NO: 39) |
| hDRAIU (exon 2 of DRA) | CTGGCGGCTTG AAGAATTTGG (SEQ ID NO: 40) | CATGATTTCCAG GTTGGCTTTGTC (SEQ ID NO: 41) | CGATTTGC-CAGC TTTGAGGCT-CAA GG (SEQ ID NO: 42) |
| 1751jxn2[1] (loss-of-allele assay, sequence present in H-2A and H-2E delete only) | CCTCACTTGGGA CCAACCCTA (SEQ ID NO: 43) | TTGTCCCAGTCA CCGTCCAT (SEQ ID NO: 44) | TGCATCTC-GAGC ACAG-GCATTTGG (SEQ ID NO: 45) |

[1]All sequences except this one are used in the gain-of-allele assay.

The selection cassette may be removed by methods known by the skilled artisan. For example, ES cells bearing the chimeric human/mouse MHC class I locus may be transfected with a construct that expresses Cre in order to remove the "loxed" selection cassette introduced by the insertion of the targeting construct. The selection cassette may optionally be removed by breeding to mice that express Cre recombinase. Optionally, the selection cassette is retained in the mice.

Targeted ES cells containing all of the modifications described in Examples 1.1-1.4 (H2-K$^{+/1666}$ MHC-II$^{+/6112}$ H2-D$^{+/delete}$ of FIG. 4) were verified using a quantitative TAQMAN® assay described above using the primer/probe sets described herein for individual modifications. An additional primer/probe set was used to determine that during cassette-deletion step, no inverted clone was created due to lox sites present in opposing orientation.

Figure 7:
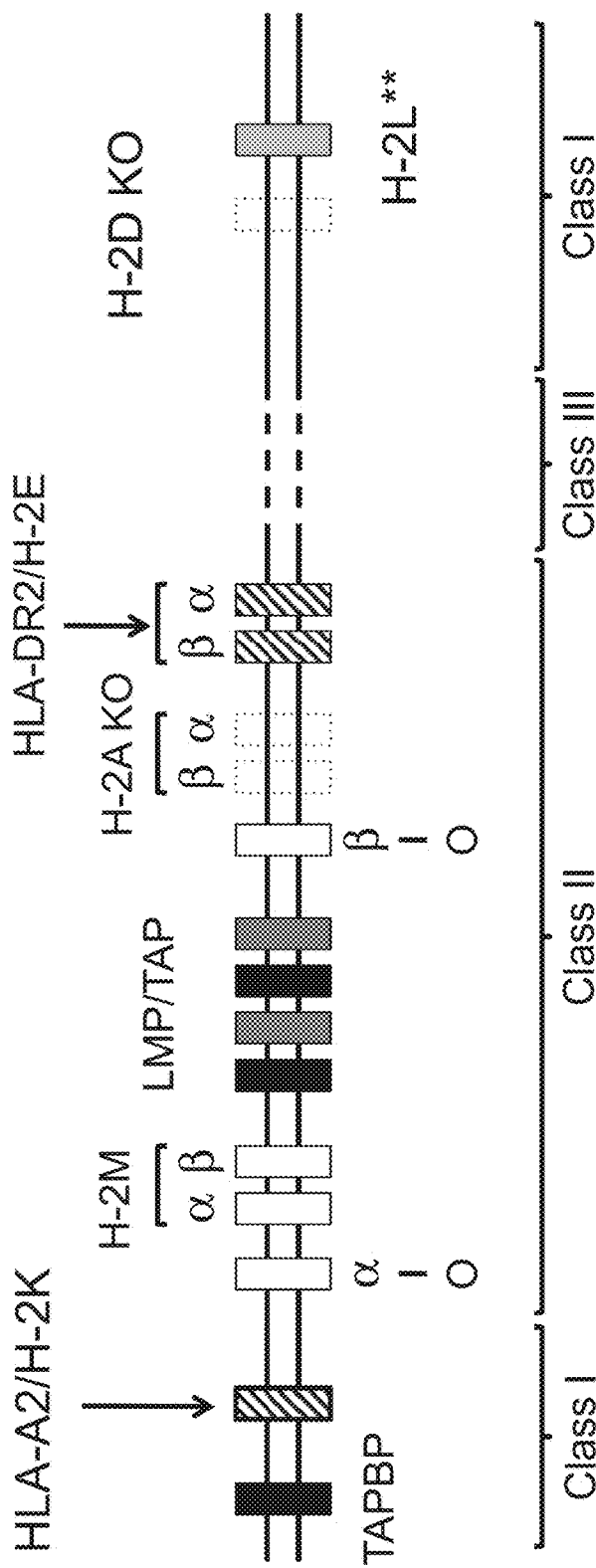
FIG. 7 is a schematic representation of exemplary genotypes of MHC loci (**) represents H-2L gene that is not present in all mouse strains), where endogenous mouse H-2K and H-2E loci were replaced by chimeric human/mouse loci, and H-2A and H-2D loci were deleted.

Targeted ES cells described above were used as donor ES cells and introduced into an 8-cell stage mouse embryo by the VELOCIMOUSE® method (see, e.g., U.S. Pat. No. 7,294,754 and Poueymirou et al. (2007) F0 generation mice that are essentially fully derived from the donor gene-targeted ES cells allowing immediate phenotypic analyses Nature Biotech. 25(1):91-99). VELOCIMICE® (F$_0$ mice fully derived from the donor ES cell) independently bearing a chimeric MHC class I and MHC II genes were identified by genotyping using a modification of allele assay (Valenzuela et al., supra) that detects the presence of the unique human gene sequences. A schematic representation of the genotype of MHC loci in the resulting mice is depicted in FIG. 7 (** represents H-2L gene which is not present in all mouse strains).

Figure 8:
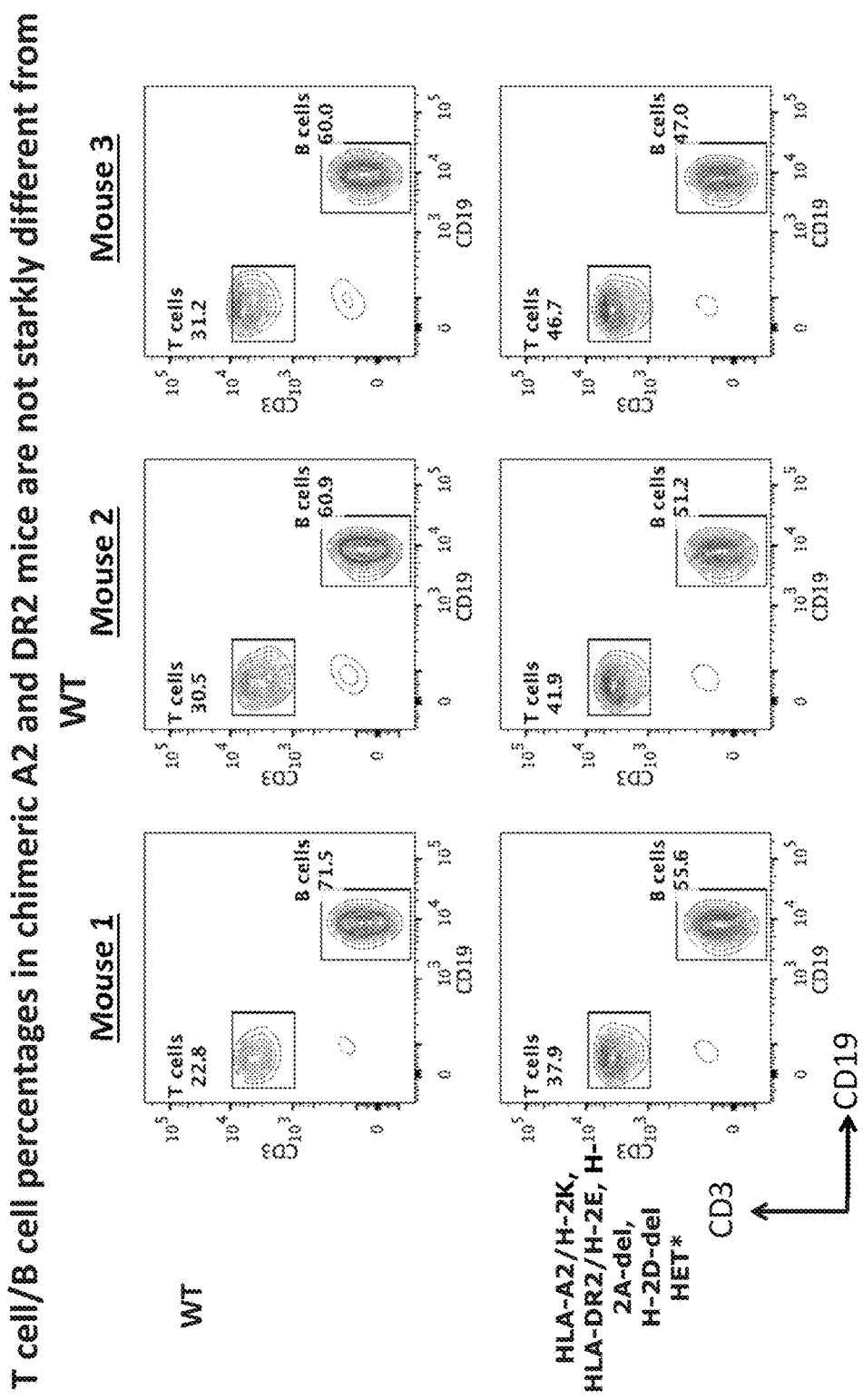
FIG. 8 depicts contour plots of percentage of mouse CD3+ T cells and CD19+ B cells in spleens from 3 wild-type (VVT) control mice and 3 chimeric A2 and DR2 mice. Cells were gated on live cells discriminated based on FSC/SSC gating. HLA-A2/H-2K, HLA-DR2/H-2E, H-2A-del, H-2D-del HET*=mice created in the genetic engineering scheme depicted in FIG. 4, also referred to in this and remaining figures as "chimeric A2 and DR2 mice."
Figure 9:
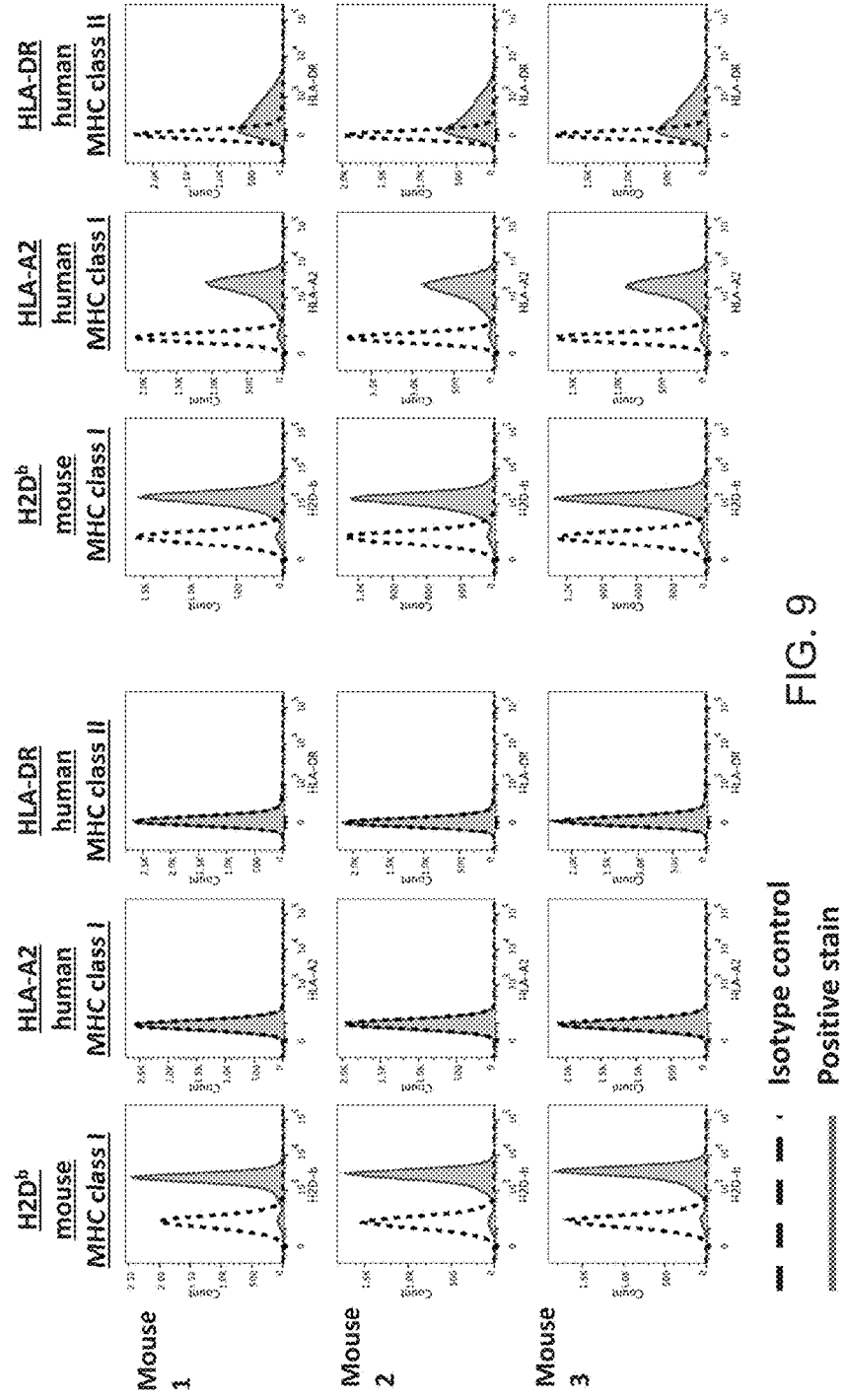
FIG. 9 depicts histograms of mouse MHC class I (H2D), human MHC class I (HLA-A2), and human MHC class II (HLA-DR) expression levels on CD19+ B cells from spleens of 3 wild-type (VVT) control mice and 3 chimeric A2 and DR2 mice.
Figure 10:
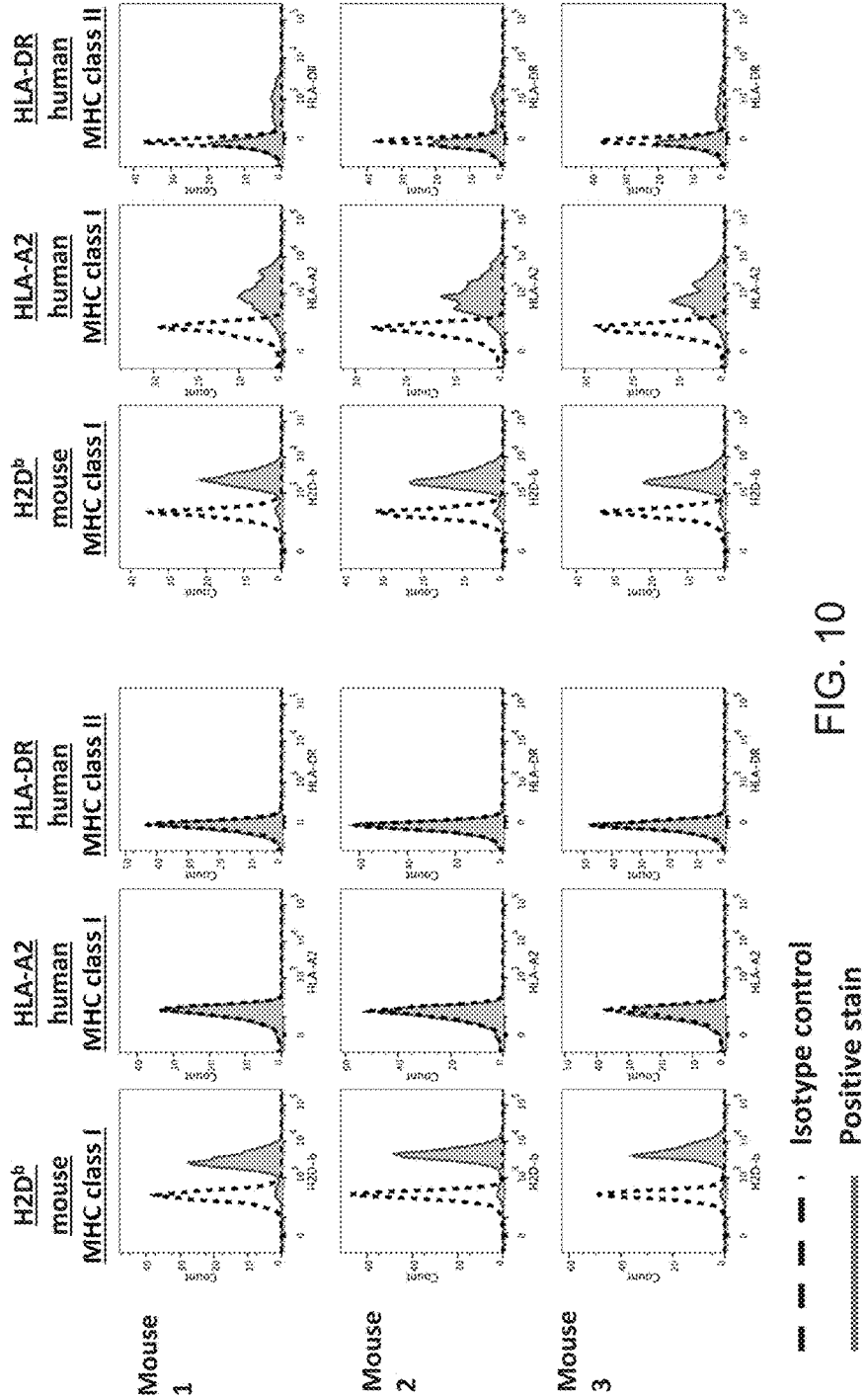
FIG. 10 depicts histograms of mouse MHC class I (H2D), human MHC class I (HLA-A2), and human MHC class II (HLA-DR) expression levels on CD14+ monocytes from spleens of 3 wild-type (WT) control mice and 3 chimeric A2 and DR2 mice.
Figure 11:
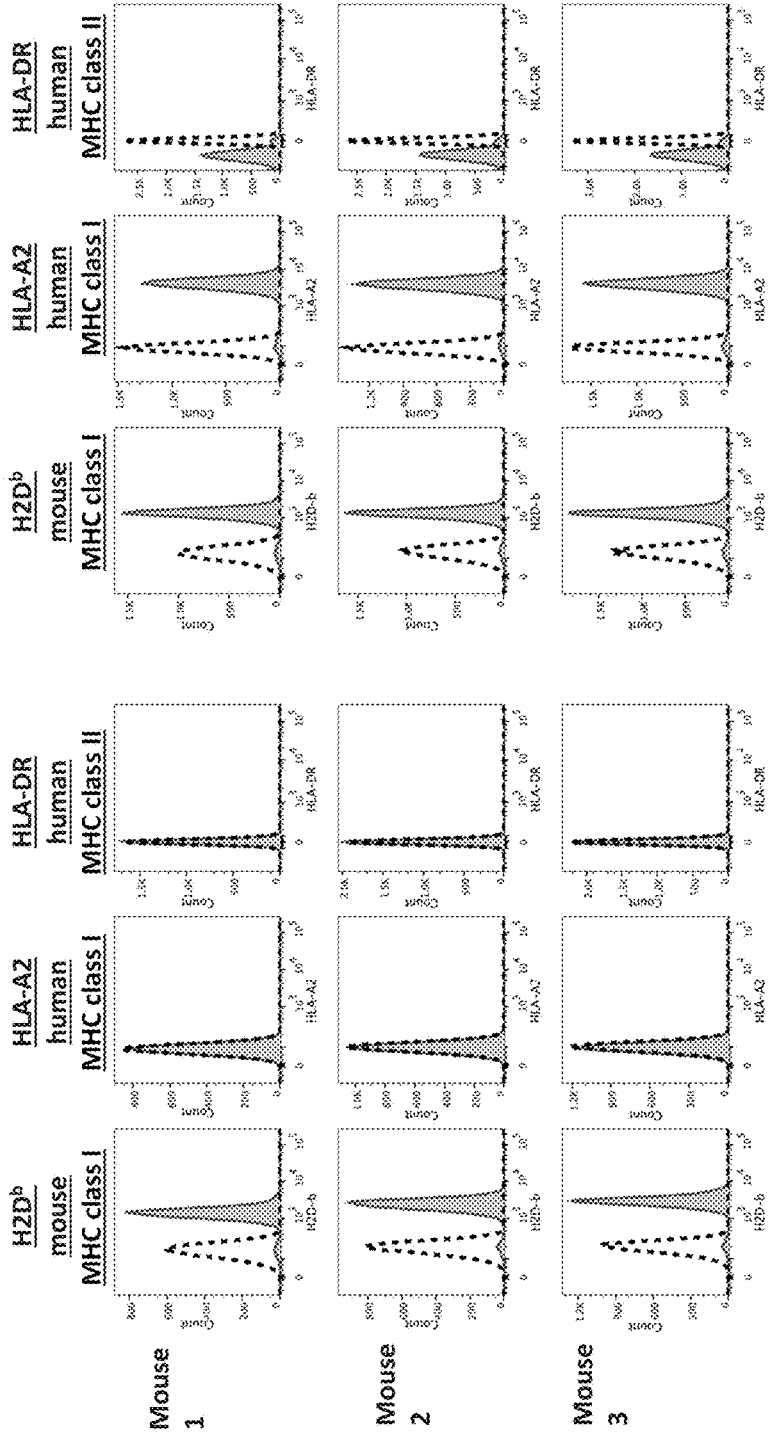
FIG. 11 depicts histograms of mouse MHC class I (H2D), human MHC class I (HLA-A2), and human MHC class II (HLA-DR) expression levels on CD3+ T cells from spleens of 3 wild-type (VVT) control mice and 3 chimeric A2 and DR2 mice.

Example 1.5: Characterization of Mice Comprising Chimeric MHC I and II Genes Spleens from WT or heterozygous humanized HLA-A2/HLA-DR2/H-2D-del mice (see mice generated on the bottom of FIG. 4 ("HLA-A2/H-2K, HLA-DR2/H-2E, H-2A-del, H-2D-del HET" or "H-2K$^{+/1666}$ MHC-II$^{+/6112}$ H2-D$^{+/delete}$" or "chimeric A2 and DR2") were harvested, and single cell suspensions were prepared. Cell surface expression of mouse MHC class I (H2D), human MHC class I (HLA-A2), and human MHC class II (HLA-DR) on CD3+ T cells, CD19+ B cells, and CD14+ monocytes were analyzed by FACS. As shown in FIG. 8, there was no significant disruption in T to B cell ratio or no significant effect on T and B cell development. Expression of human HLA-A2 and HLA-DR were detectable on the surface of CD19+ B cells and monocytes (FIGS. 9 and 10). Expression of human HLA-A2, but not HLA-DR, was detectable on the surface of CD3+ T cells (FIG. 11), as MHC II is only expressed on antigen-presenting cells.

Equivalents

Those skilled in the art will recognize, or be able to ascertain using no more than routine experimentation, many equivalents of the specific embodiments of the invention described herein. Such equivalents are intended to be encompassed by the following claims.

Entire contents of all non-patent documents, patent applications and patents cited throughout this application are incorporated by reference herein in their entirety.

What is claimed is:

1. A genetically modified mouse whose genome comprises at an endogenous MHC locus:
a first nucleotide sequence encoding a chimeric human/mouse MHC I polypeptide that comprises α1, α2 and α3 domains of a human MHC I polypeptide operably linked to transmembrane and cytoplasmic domains of a mouse MHC I polypeptide,
a second nucleotide sequence encoding a chimeric human/mouse MHC II α polypeptide that comprises α1 and α2 domains of a human MHC II α polypeptide operably linked to transmembrane and cytoplasmic domains of a mouse MHC II α polypeptide, and
a third nucleotide sequence encoding a chimeric human/mouse MHC II β polypeptide that comprises β1 and β2 domains of a human MHC II β polypeptide operably linked to transmembrane and cytoplasmic domains of a mouse MHC II β polypeptide,
wherein the mouse expresses the chimeric human/mouse MHC I, MHC II α and MHC II β polypeptides from the endogenous MHC locus, and
wherein all genes encoding classical endogenous mouse MHC I and MHC II proteins that are expressed on a cell surface are functionally inactivated.

2. The mouse of claim 1, wherein the first nucleotide sequence is located at an endogenous mouse MHC I locus, the second nucleotide sequence is located at an endogenous mouse MHC II α locus, and the third nucleotide sequence is located at an endogenous mouse MHC II β locus.

3. The mouse of claim 1, wherein the first, second and/or third nucleotide sequence(s) are operably linked to endogenous mouse regulatory elements.

4. The mouse of claim 1, wherein the human MHC I polypeptide is selected from the group consisting of HLA-A, HLA-B, and HLA-C.

5. The mouse of claim 1, further comprising at an endogenous mouse β2 microglobulin locus a nucleotide sequence encoding a human or humanized β2 microglobulin polypeptide, wherein the mouse expresses the human or humanized β2 microglobulin polypeptide.

6. The mouse of claim 1, wherein the first nucleotide sequence is operably linked to endogenous mouse MHC I promoter and regulatory elements, the second nucleotide sequence is operably linked to endogenous mouse MHC II α promoter and regulatory elements, and the third nucleotide sequence is operably linked to endogenous mouse MHC II β promoter and regulatory elements.

7. The mouse of claim 1, wherein the human MHC II α and β polypeptides are α and β polypeptides, respectively, of a human HLA class II protein selected from the group consisting of HLA-DR, HLA-DQ, and HLA-DP.

8. The mouse of claim 7, wherein the human HLA class II protein is a human HLA-DR protein.

9. The mouse of claim 1, wherein the mouse MHC I polypeptide is H-2K, H-2D, or H-2L.

10. The mouse of claim 9, wherein the mouse MHC I polypeptide is H-2K.

11. The mouse of claim 7, wherein the mouse MHC II α and β polypeptides are α and β polypeptides, respectively, of a mouse MHC II protein selected from H-2E and H-2A.

12. The mouse of claim 11, wherein the mouse MHC II protein is H-2E.

13. The mouse of claim 12, wherein the mouse endogenous gene encoding a H-2A polypeptide is functionally inactivated.

14. The mouse of claim 1, wherein the first nucleotide sequence encodes a chimeric HLA-A/H-2K polypeptide, the second nucleotide sequence encodes an α chain of a chimeric HLA-DR/H-2E polypeptide, and the third nucleotide sequence encodes a β chain of a chimeric HLA-DR/H-2E polypeptide, and wherein the mouse expresses HLA-A/H-2K and HLA-DR/H-2E proteins.

15. The mouse of claim 14, wherein the first nucleotide sequence is located at an endogenous mouse H-2K locus and wherein the mouse lacks all or part of an endogenous H-2D gene and/or all or part of an endogenous mouse H-2L gene.

16. The mouse of claim 14, wherein the second nucleotide sequence is located at an endogenous H-2E α locus and the third nucleotide sequence is located at an endogenous H-2E β locus gene, and wherein the mouse lacks all or part of an endogenous mouse H-2A gene.

17. The mouse of claim 15, wherein the second nucleotide sequence is located at an endogenous H-2E α locus and the third nucleotide sequence is located at an endogenous H-2E β locus, and wherein the mouse lacks all or part of an endogenous mouse H-2A gene.

18. The mouse of claim 1, wherein the classical endogenous mouse MHC I proteins that are expressed on the cell surface are H-2K, H-2D, and H-2L, and wherein the classical endogenous mouse MHC II proteins that are expressed on the cell surface are H-2A and H-2E.

* * * * *